US007427269B2

United States Patent
George et al.

(10) Patent No.: US 7,427,269 B2
(45) Date of Patent: Sep. 23, 2008

(54) ACCURATE METHOD TO CHARACTERIZE AIRWAY NITRIC OXIDE USING DIFFERENT BREATH-HOLD TIMES INCLUDING AXIAL DIFFUSION OF NITRIC OXIDE USING HELIOX AND BREATH HOLD

(75) Inventors: Steven C. George, Irvine, CA (US); Hye-Won Shin, Irvine, CA (US); Peter Condorelli, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 139 days.

(21) Appl. No.: 11/636,027

(22) Filed: Dec. 8, 2006

(65) Prior Publication Data

US 2007/0149891 A1    Jun. 28, 2007

Related U.S. Application Data

(60) Provisional application No. 60/749,859, filed on Dec. 12, 2005.

(51) Int. Cl.
*A61B 5/08* (2006.01)
(52) U.S. Cl. .................. 600/532; 600/529; 600/533
(58) Field of Classification Search .......... 600/529–543
See application file for complete search history.

(56) References Cited

U.S. PATENT DOCUMENTS 5,922,610 A * 7/1999 Alving et al. ............... 436/116

6,302,851 B1 * 10/2001 Gedeon ...................... 600/538
6,866,637 B2 * 3/2005 George et al. ............... 600/532

OTHER PUBLICATIONS

Kharitonov SA and Barnes PJ. Nasal Contribution to exhaled nitric oxide during exhalation against resistance or during breath holding. Thorax 52:540-544, 1997.*
Shin HW, Condorelli P, and George SC. A new and more accurate technique to characterize airway nitric oxide using different breath-hold times. J Appl Physiol 98:1869-1877, 2005.*
Shin HW, Condorelli P, George SC. Examining axial diffusion of nitric oxide in the lungs using heliox and breath hold. J Appl Physiol 100: 623-630, 2006.*

* cited by examiner

*Primary Examiner*—Robert L. Nasser, Jr.
*Assistant Examiner*—Karen E Toth
(74) *Attorney, Agent, or Firm*—Daniel L. Dawes

(57) ABSTRACT

An apparatus and method to characterize NO gas exchange dynamics in human lungs comprising the steps of: (1) performing a series of breath hold maneuvers of progressively increasingly breath hold times, each breath hold maneuver comprising a) inhaling a gas, b) holding a breath for a selected time duration, and c) exhaling at a flow rate which is uncontrolled but which is effective to ensure evacuation of the airway space and (2) measuring airway NO parameters during consecutive breath hold maneuvers. As a result disease states of the lungs are diagnosed using the measured airway NO parameters.

32 Claims, 25 Drawing Sheets

ACCURATE METHOD TO CHARACTERIZE AIRWAY NITRIC OXIDE USING DIFFERENT BREATH-HOLD TIMES INCLUDING AXIAL DIFFUSION OF NITRIC OXIDE USING HELIOX AND BREATH HOLD

RELATED APPLICATIONS

The present application is related to U.S. Provisional Patent Application, Ser. No. 60/749,859 filed on Dec. 12, 2005, which is incorporated herein by reference and to which priority is claimed pursuant to 35 USC 119.

BACKGROUND OF THE INVENTION

1. Field of the Invention

The invention relates to the field of methodologies and apparatus used to characterize airway nitric oxide using different breath-hold times to characterize region-specific inflammation or pulmonary disease states.

2. Description of the Prior Art

Exhaled nitric oxide (NO) arises from both airway and alveolar regions of the lungs, which provides an opportunity to characterize region-specific inflammation. Current methodologies rely on vital capacity breathing maneuvers and controlled exhalation flow rates, which can be difficult to perform, especially for young children and individuals with compromised lung function. In addition, recent theoretical and experimental studies demonstrate that gas-phase axial diffusion of NO has a significant impact on the exhaled NO signal.

Nitric oxide can be detected in exhaled breath and is a potential noninvasive index of lung inflammation. Nitric oxide (NO) can be detected in the exhaled breath, and the concentration, FeNO, may reflect the inflammatory status of the lungs. However, NO exchange dynamics in the lungs are not yet fully developed, due primarily to the unique gas exchange characteristics of NO that include both airway and alveolar contributions. Current methodologies for partitioning exhaled NO into airway and alveolar contributions rely on vital capacity breathing maneuvers, which utilize a controlled exhalation flow rate, or a tidal breathing pattern. The techniques characterize the alveolar region with an alveolar concentration ($Ca_{NO}$) and the airway region with two parameters, the airway diffusing capacity ($Daw_{NO}$) and either the airway wall concentration ($C_{awNO}$) or the maximum airway wall flux ($J'aw_{NO}$; equal to the product $Daw_{NO} \times Caw_{NO}$). The techniques have been used successfully to characterize NO gas exchange dynamics for healthy subjects, as well as a wide range of lung diseases.

Important limitations remain in the characterization of NO exchange for both the experimental breathing maneuvers and the theoretical models. Early models of NO exchange neglected axial diffusion of NO in the gas phase, as well as the increasing cross-sectional area of the airway tree with increasing airway generation (i.e., trumpet shape). These simplifications generated errors in the estimation of $Caw_{NO}$ and $J'aw_{NO}$. In addition, the variance of $Daw_{NO}$ was larger than other parameters, and the accuracy depends on the residence time of the air in the airway compartment. A unique challenge in determining $Daw_{NO}$ is the need to sample very low (<50 ml/s) exhalation flows. $Daw_{NO}$ can only be measured if a very low exhalation flow rate (about 50 ml/s) is sampled. This requires long (about 20 s) and controlled (i.e., constant flow) exhalation phases, which can be difficult to perform for young children and subjects with compromised lung function. Importantly, $Daw_{NO}$ may potentially provide unique structural information about the airways in lung diseases such as asthma. Accurate estimation of $Daw_{NO}$ is particularly interesting because initial studies suggest that it is elevated in asthma but may be independent of steroid use, unlike $Fe_{NO}$ and $Caw_{NO}$.

In addition, the most widely used analytical methods invoke a two-compartment model, which assumes a simple cylinder geometry to represent the airway anatomy, and neglects gas-phase axial diffusion of NO. Although these assumptions preserve mathematical simplicity, they likely generate significant errors in characterizing NO exchange.

Therefore, what is needed is 1) a technique that is simple to perform and focuses on determining airway NO parameters ($Caw_{NO}$, $Daw_{NO}$, and $J'aw_{NO}$), and 2) which compensates for important sources of errors, such as axial diffusion and the branching structure of the airway tree, that exist in some of the currently used methods to characterize NO exchange in the lung.

BRIEF SUMMARY OF THE INVENTION

We have developed a new technique to characterize airway NO, which requires a series of progressively increasing breath-hold times followed by exhalation of only the airway compartment. Using our new technique, we determined values (means±SE) in healthy adults (20-38 yr, n=8) for the airway diffusing capacity [$4.5 \pm 1.6$ pl s$^{-1}$ parts per billion (ppb)$^{-1}$], the airway wall concentration ($1,340 \pm 213$ ppb), and the maximum airway wall flux ($4,350 \pm 811$ pl/s). The new technique is simple to perform, and application of this data to simpler models with cylindrical airways and no axial diffusion, yields parameters consistent with previous methods.

Inclusion of axial diffusion as well as an anatomically correct trumpet-shaped airway geometry results in significant loss of NO from the airways to the alveolar region, profoundly impacting airway NO characterization. In particular, the airway wall concentration is more than an order of magnitude larger than previous estimates in healthy adults and may approach concentrations (about 5 nM) that can influence physiological processes such as smooth muscle tone in disease states such as asthma.

Consider now an examination of axial diffusion of NO in the lungs using heliox and air. Exhaled nitric oxide (NO) is highly dependent on exhalation flow; thus exchange dynamics of NO have been described by multicompartment models and a series of flow-independent parameters that describe airway and alveolar exchange. Because the flow-independent NO airway parameters characterize features of the airway tissue (e.g., wall concentration), they should also be independent of the physical properties of the insufflating gas. We measured the total mass of NO exhaled ($A_{I,II}$) from the airways after five different breath-hold times (5-30 s) in nine healthy adults (21-38 yr, n=9) using air and heliox as the insufflating gas, and then modeled $A_{I,II}$ as a function of breath-hold time to determine airway NO exchange parameters. Increasing breath-hold time results in an increase in $A_{I,II}$ for both air and heliox, but $A_{I,II}$ is reduced by a mean (SD) of 31% (SD 6) (P<0.04) in the presence of heliox, independent of breath-hold time. However, mean (SD) values (air, heliox) for the airway wall diffusing capacity [3.70 (SD 4.18), 3.56 pl s$^{-1}$ ppb$^{-1}$ (SD 3.20)], the airway wall concentration [1,439 (SD 487), 1,503 ppb (SD 644>)], and the maximum airway wall flux [4,156 (SD 2,502), 4,412 pl/s (SD 2,906)] using a single-path trumpet shaped airway model that considers axial diffusion were independent of the insufflating gas (P>0.55). We conclude that a single-path trumpet model that considers axial diffusion captures the essential features of airway wall NO exchange and confirm earlier reports that the airway wall concentration in healthy adults exceeds 1 ppm and thus approaches physiological concentrations capable of modulating smooth muscle tone.

In summary, the illustrated embodiment is a method to characterize NO gas exchange dynamics in human lungs comprising the steps of: (1) performing a series of breath hold maneuvers of progressively increasingly breath hold times, each breath hold maneuver comprising a) inhaling a gas, b) holding a breath for a selected time duration, and c) exhaling at a flow rate which is uncontrolled but which is effective to ensure evacuation of the airway space and (2) measuring airway NO parameters during consecutive breath hold maneuvers. As a result disease states of the lungs are diagnosed using the measured airway NO parameters.

The method further comprises the step of maintaining a predetermined positive pressure during the breath hold and exhalation to prevent nasal contamination of the measured airway NO parameters.

In one embodiment the step of maintaining a predetermined positive pressure during the breath hold and exhalation to prevent nasal contamination comprises the step of maintaining a positive pressure of 5 cm $H_2O$ or more.

In one embodiment the step of exhaling at a flow rate evacuates the airway space in 2 seconds or less.

In one embodiment the step of exhaling at a flow rate evacuates the airway space comprises the step of exhaling at a rate of 300 ml/s or more.

In one embodiment the step of performing the series of breath hold maneuvers of progressively increasingly breath hold times comprises the step of performing a series of breath hold maneuvers with breath hold times of having increasing durations of 5 seconds over the previous breath hold.

In one embodiment the step of performing the series of breath hold maneuvers with breath hold times of having increasing durations of 5 seconds over the previous breath hold comprises the step of performing a series of breath hold maneuvers with breath hold times of having 5-, 10-, 15-, 20-, and 30-second breath holds.

In one embodiment the step of measuring airway NO parameters during consecutive breath hold maneuvers comprises the step of measuring the indexes of NO exchange dynamics and spirometry.

In one embodiment the step of measuring spirometry comprises the step of measuring forced vital capacity and forced expiratory volume in 1 second.

In one embodiment the step of exhalation is characterized as comprised of three temporal phases I, II and II and where the step of measuring the indexes of NO exchange dynamics and spirometry comprises the step of measuring:

maximum observed concentration of NO, $C_{peakNO}$,
width of phases I and II of exhalation, $W_{50}$,
total exhaled volume of NO during phases I and II, $V_{I,II}$, and/or
total mass or volume of NO in phases I and II, $A_{I,II}$.

In one embodiment a model of an entire airway tree of the lungs is assumed and further the method comprises the step(s) of: determining diffusing capacity of NO in an entire airway tree of the lungs, $Daw_{NO}$; determining airway wall concentration of NO, $Caw_{NO}$; and/or determining maximum total volumetric flux of NO from the entire airway tree, $J'aw_{NO}$ from the measured airway NO parameters.

In one embodiment the assumed model of an entire airway tree of the lungs comprises a model including a trumpet geometry of the airway of the lungs and gas phase axial diffusion of NO occurs.

In one embodiment the step of inhaling a gas comprises inhaling heliox in a sufficient amount to enhance NO diffusion in the lungs to modulate airway smooth muscle tone, e.g. inhaling sufficient amounts of heliox to activate soluble guanylate cyclase in airway smooth muscle tissue.

The scope of the invention further expressly contemplates an apparatus for performing each of the embodiments of the above breath hold methodology.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
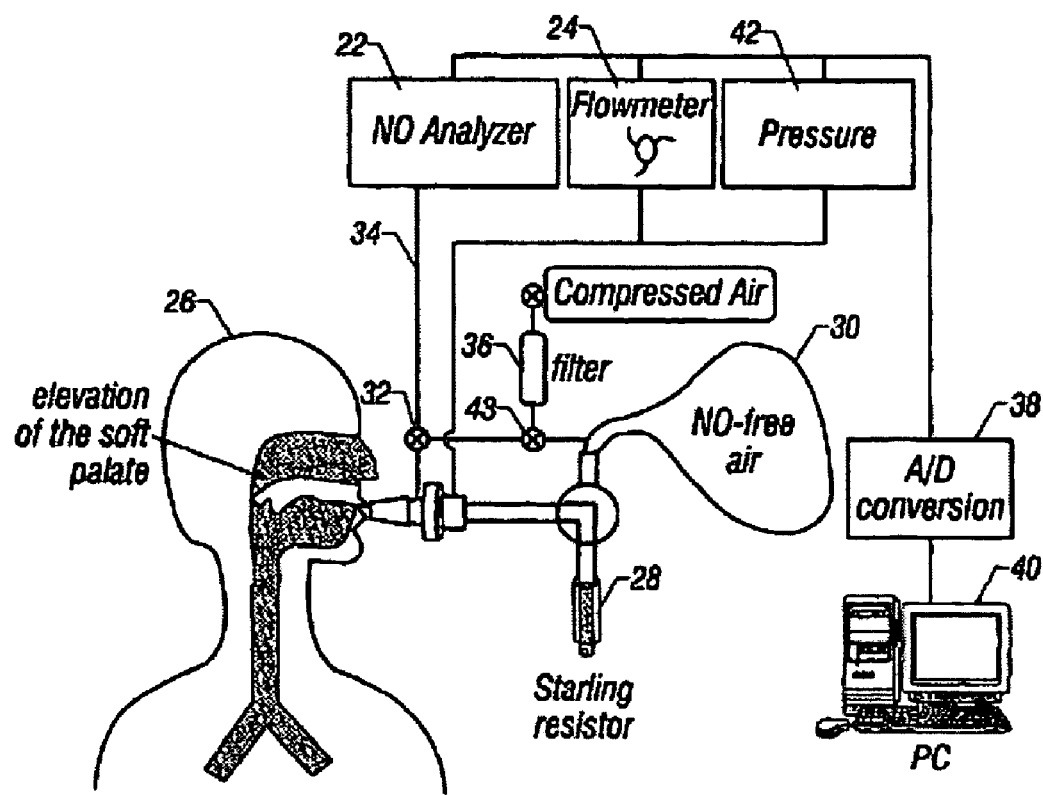
FIG. 1 is a block diagram of the apparatus in which the method of the illustrated embodiment is practiced.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

To provide a technique that is simple to perform and focuses on determining airway NO parameters ($Caw_{NO}$, $Daw_{NO}$, and $J'aw_{NO}$), and 2) which compensates for important sources of errors, such as axial diffusion and the branching structure of the airway tree, that exist in some of the currently used methods to characterize NO exchange in the lung, the illustrated embodiment utilizes a series of different breath-hold times (5-30 s) and analyzes only the expired air from the airways, thus shortening and simplifying the analysis of the exhalation phase. When axial diffusion is neglected, and a cylindrical airway geometry is used, the airway NO parameters determined from the new technique are consistent with those determined from a previously described single-breath technique. However, when axial diffusion and a trumpet-shaped geometry are considered, airway NO parameters are significantly different. In particular, $Caw_{NO}$ is increased by more than 14-fold to compensate for losses of NO from the airways to the alveolar region due to axial diffusion. This finding has important implications pertaining to physiological processes in disease states such as smooth muscle tone in asthma.

The following are definitions of various quantities in and with which the illustrated embodiments are described:

$A_{I,II}$—Area under the curve in phases I and II of the exhaled NO profile [parts per billion (ppb)/ml]

$A_c(z)$—Cross-sectional area of airway space (cm²)

$Ca_{NO}$—Mixed or average fractional concentration of NO in the gas phase of the alveolar region (ppb). A steady-state concentration is achieved for breath-hold or exhalation times of about 10 s.

$Caw_{NO}$—Airway wall concentration of NO (ppb)

$Ce_{NO}$—Exhaled NO concentration at the mouth (ppb)

$Cin_{NO}$—Exhaled NO concentration (ppb) which enters the analytical instrument $C_{NO}$—Exhaled NO concentration (ppb) in the gas phase of the airways $Cobs_{NO}$—Exhaled NO concentration (ppb) observed from the analytical instrument $Cs_{NO}$—Exhaled NO concentration (ppb) which enters the sampling line leading to the analytical instrument $Cpeak_{NO}$—The maximum or peak exhaled NO concentration (ppb) observed by the analytical instrument $Daw_{NO}$—Diffusing capacity (ml/s) of NO in the entire airway tree, which is expressed as the volume of NO per second per fractional concentration of NO in the gas phase [ml NO s$^{-1}$ (ml NO/ml gas)$^{-1}$] and is equivalent to pl s$^{-1}$ ppb$^{-1}$ $D_{NO, air}$—Molecular diffusivity (diffusion coefficient) of NO in air (cm²/s)

$J'aw_{NO}$—Maximum total volumetric flux (ppb ml s$^{-1}$ or pl/s) of NO from the airways $J_{axial}$—The rate of axial diffusion of NO (pl/s) across the boundary of the airway compartment and alveolar compartment defined by Fick's first law of diffusion RMS Root mean square error between experimental data and model prediction $V_{I,II}$—Exhaled volume in phases I and II of the exhalation profile (ml)

Vaw—Volume (ml) of the airway tree defined by the cumulative volume of airway generations 0-17 based on Weibel or the subjects ideal body weight (lbs.) plus age in years z—Axial position in the lungs (cm)

Table 1 summarizes experiment subjects. Eight healthy adults (age 20-38 yr, two women) participated in the study. All subjects had a ratio of forced expiratory volume in 1 s to forced vital capacity of >0.75 at the time of testing. In addition, all subjects had no history of smoking at any time, and no history of cardiovascular, pulmonary, or neurological diseases.

Each subject performed a series of breath-hold maneuvers (5-, 10-, 15-, 20-, and 30-s breath hold), followed by an exhalation in which the flow rate was not controlled but was generally >300 ml/s to ensure evacuation of the airway space in <2 s. A positive pressure >5 cm H$_2$O was maintained during the breath hold and exhalation to prevent nasal contamination.

In addition to the breath holding protocol of the illustrated embodiment, each subject performed a single-breath maneuver (a 20-s breath hold followed by a decreasing flow rate maneuver) to determine airway NO parameters as a "gold standard" for comparison to our new technique. After measuring the indexes of NO exchange dynamics, general spirometry, including forced vital capacity and forced expiratory volume in 1 s, was measured in all subjects (Vmax229; Sensormedics, Yorba Linda, Calif.) by using the best performance as shown in Table 1 from three consecutive maneuvers.

A schematic of the experimental apparatus is shown in FIG. 1, which is a block diagram of the experimental setup used to collect the exhalation profiles. The identical apparatus, used differently, is disclosed in U.S. Pat. No. 6,866,637, which is incorporated herein by reference. The flow, pressure, and NO analog signals are captured by the analytical instruments and converted to a digital signal. A series of valves allows NO-free air to be stored in a mylar bag 30 for inspiration. During the breathhold, the NO analyzer 22 samples from the NO-free air reservoir 30, and the subject maintains a positive pressure of >5 cm H$_2$O by attempting to exhale against a closed valve 43. As exhalation begins, the NO analyzer 22 then samples from the exhalate. Then, for a bolus of gas that reaches the sampling port of the analyzer 22 at time t+$t_{ds}$, $t_{ds}$ and $T_{res}$ can be estimated using backward integration of the expiratory flow signal if $V_{ds}$ and $V_{air}$ are known. $V_{ds}$ is approximated from the volume the subject needs to expire prior to observing a change in $C_{exh}$ (after the signals have been synchronized). A first approximation of $V_{air}$ will be the physiological dead space in ml, as approximated by the weight (assuming normal body fat) of the subject in pounds plus the age of the subject in years.

The protocol was performed using the system schematically shown in FIG. 1. The subjects 26 performed a series of oral exhalation breathing maneuvers against a small resistance (>5 cm H$_2$O) for the isolation of the nasal cavity. The subjects 26 first performed vital capacity maneuvers. The subjects 26 then performed a series of exhalations following progressively longer periods of breath holding. A nose-clip is placed on the subjects nose to prevent any nasal flow of of air, and the subjects is asked to inspire NO-free air from the reservoir 30 to total lung capacity until they cannot inhale any additional air. The expiratory valve 43 is then turned such that the subject cannot expire any air. Thus, the patient is holding their breath. During the breathhold, the subject 26 exerts an expiratory effort against a closed valve 43 to maintain a positive pressure of >5 cm H$_2$O in the expiratory line 44, and the NO sampling line 34 samples air from the zero NO reservoir 30. Since exhalation rates were free or uncontrolled, the use of Starling resistor 28 was omitted. At the end of the desired breathhold time, or just prior to exhalation, the valve 32 on the NO sampling line 34 is changed to sample from the exhaled breath and the exhalation valve 43 is opened allowing the patient 26 to expire. The expiratory flow rate progressively decreases during the exhalation from an initial value of about 300 ml/s (about 6% of the vital capacity per second) to about 50 ml/s (about 1% of the vital capacity per second). The subject expires until no more air can be expelled. This constitutes the end of the breathing maneuver.

NO concentration was measured using a chemiluminescence NO analyzer 22 (NOA280, Sievers, Inc., Boulder, Colo.). An operating reaction cell pressure was maintained at 7.5 mm Hg, which provided a sampling flow rate of 250 ml/min. The analyzer 22 was calibrated on a daily basis using a certified NO gas (25 ppm in $N_2$, INO max Sensormedics, CA). The zero point calibration was performed with an NO filter 36 (Sievers, Inc., Boulder, Colo.). Due to a small drift in the calibration of the analyzer 22 during the day, we performed zero point calibration immediately prior to the collection of a profile. The flow rate was measured using a pneumotachometer 24 (RSS100, Hans Rudolph Inc., Kansas City, Mo.). The pneumotachometer 24 was calibrated daily and was set to provide the flow in units of ml/s STPD (Standard Pressure Temperature Dry). Pressure was measured by a pressure meter 42 model RSS100 manufactured by Hans Rudolph Inc. (Kansas City, Mo.). The analog signals of flow and NO were digitized using an A/D card 38 at a rate of 50 Hz and stored on a personal computer 40 for further analysis. While computer 40 is arranged and configured by conventional programming to perform the functions disclosed in this specification, it is to be expressly understood that computer 40 may be substituted by equivalent means, such as logic circuits, digital signal processors and other analog and/or digital signal processing circuitry.

Figure 2:
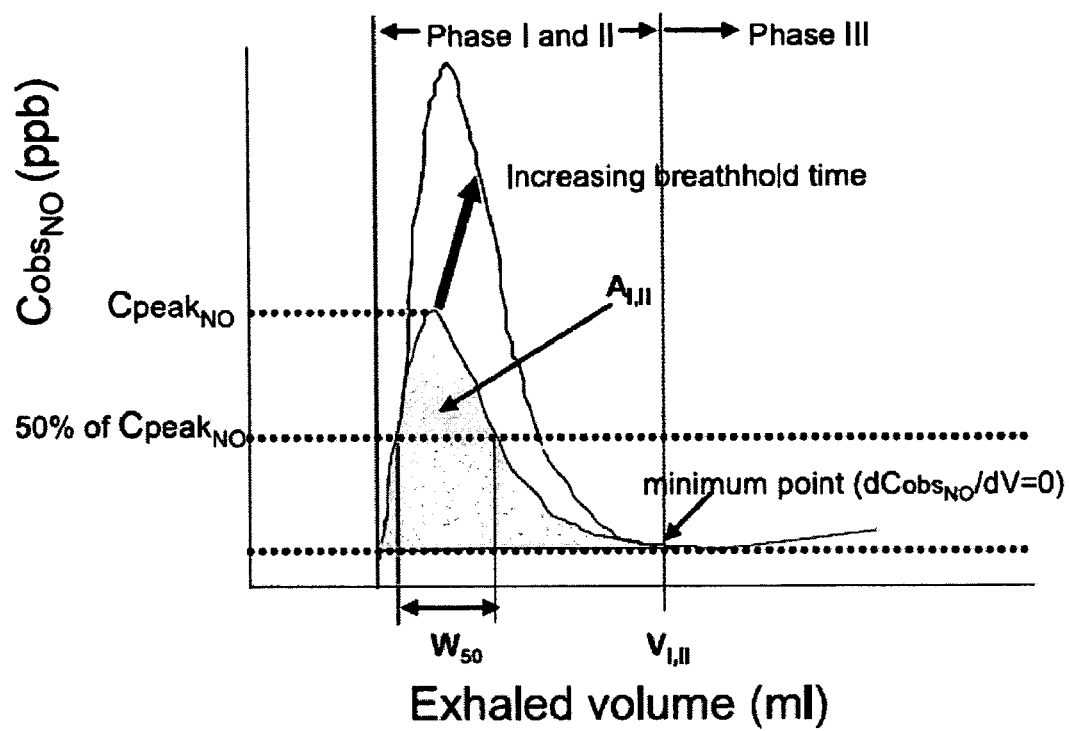
FIG. 2 is a graph which depicts model-independent parameters characteristic of the observed exhalation profile in phases I and II: $C_{peakNO}$, maximum concentration of nitric oxide (NO) in phases I and II; $W_{50}$, width of phase I and II peak calculated by taking the volume at which the exhaled concentration is larger than 50% of $C_{peakNO}$; $V_{I,II}$, volume of phases I and II; $A_{I,II}$, total mass of NO (area under the curve, which is shown as a shaded region) in phases I and II; $C_{obsNO}$, exhaled NO concentration observed from the analytical instrument; ppb, parts per billion. The distinction between phase I and II and phase III is the point of zero slope (minimum point) in the exhalation profile. The top curve is a schematic representation of the exhalation profile for a larger breath-hold time.

Experimental exhalation profiles following breath hold were characterized empirically (model independent) by the peak or maximum observed concentration in phases I and II as shown in FIG. 2 of the exhalation profile ($Cpeak_{NO}$); the width of phases I and II ($W_{50}$) defined as the exhaled volume in which the NO concentration was >50% of $Cpeak_{NO}$; the total exhaled volume of phases I and II ($V_{I,II}$); and the total mass or volume of NO (area under the curve) in phases I and II ($A_{I,II}$). Each of these parameters are defined in FIG. 2.

Mathematical models to estimate airway NO parameters were developed for four cases: 1) cylinder airway in the absence of axial diffusion (C); 2) cylinder airway in the presence of axial diffusion (C-AD); 3) trumpet airway in the absence of axial diffusion (T); and 4) trumpet airway in the presence of axial diffusion (T-AD). The salient features of each model are presented below.

Figure 3A:
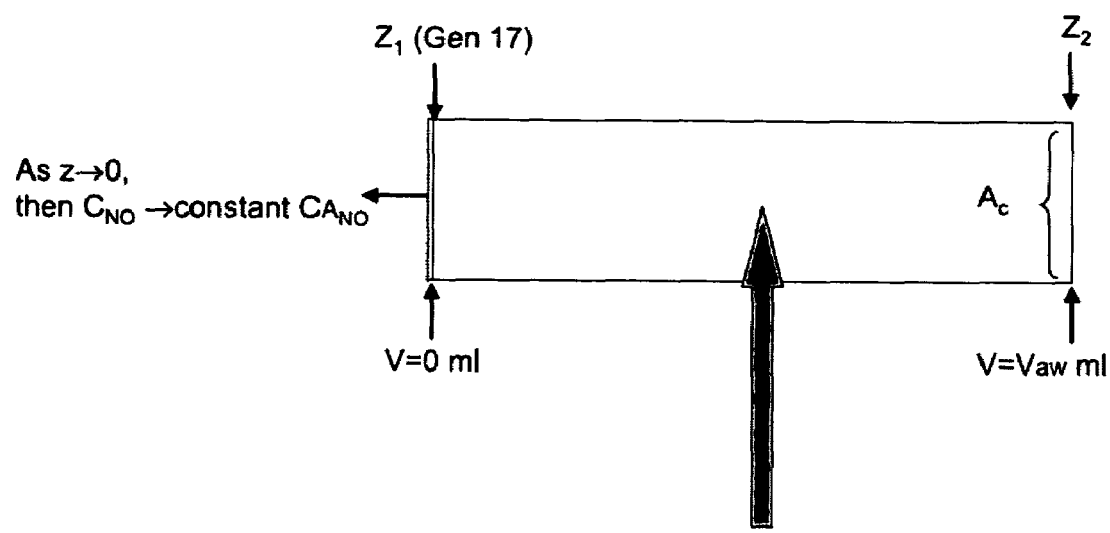
FIGS. 3a and 3b are schematics of the human airway tree through 17 generations based on a cylinder model in FIG. 3a and a trumpet model in FIG. 3b. The trumpet model is based on the symmetric bifurcating structure of Weibel. The cumulative crosssectional area for any axial position, z, for the trumpet is calculated based on the cumulative cross-sectional area of all of the airways at that position. As z approaches zero, exhaled NO concentration in the gas phase of the airways ($C_{NO}$) approaches the constant alveolar concentration ($Ca_{NO}$). For simplicity, $Ca_{NO}$ is set to zero for the current simulations. Ac, cross-sectional area of airway space.

In the cylinder model, the airway tree is represented by a perfect cylinder as depicted in FIG. 3A and is consistent with prior art analytical methods to characterize NO exchange. The impact of axial diffusion was quantified by comparing simulations which excluded (C) and included (C-AD) axial diffusion. The mathematical details are presented below. The performance of the illustrated embodiments were evaluated by comparing airway model parameters, determined using model C, to those determined using a single-breath technique, which also employed model C. For each subject, we characterized airway geometry by appropriately scaling the lengths and diameters of Weibel's data of the human airway tree, based on the conducting airway volume (Vaw) of generations 0-17, and assuming a symmetric branching pattern. The scaling procedure is based on the ratio of each subject's vital capacity to the vital capacity of the Weibel lung and yields values for Vaw that are not statistically different than estimating Vaw using the subject's ideal body weight (lbs.) plus age in yr (24) as summarized in Table 1. The length of the cylinder is set to the cumulative length of generations 0-17, which fixes the constant cross-sectional area by matching Vaw shown in FIG. 3A. Although $Ca_{NO}$ has been shown by many investigators to be nonzero, the values are generally <2 ppb, which are much lower than those observed in the airway tree during the breath-hold times of the current technique; thus $Ca_{NO}$ is set to zero as one of the boundary conditions.

A detailed description of the mathematical model is as follows. The unsteady-state diffusion equation during breath hold in the airway (through generation 17) compartment is derived by the following mass balance for NO, which includes the relationship between airway cross-sectional area and axial position $$\frac{dC_{NO}}{dt} = D_{NO,air}\frac{d}{dz}\left(A_c\frac{dC_{NO}}{dz}\right) - \frac{Daw_{NO}}{V_{air}}(C_{NO} - Caw_{NO}) \quad (A1)$$

$$A_c = A_{c,1}\left(\frac{Z}{Z_1}\right)^{-m} \quad (A2)$$

where $D_{NO,air}$ is molecular diffusivity of NO in air. The left side of Eq. A1 represents NO accumulation in the gas phase. The first term on the right side of Eq. A1 represents axial diffusion with variable cross sectional area, and the second term represents the radial flux of NO from the airways. Beyond generation 17, the airways and alveoli are lumped together to become a single boundary. For Eq. A2, m=0 for a cylinder, and m=2 for the best-fit trumpet-shaped airway (See FIG. 3B). The initial condition for Eq. A1 is $$C_{NO}(z, t=0)=0,$$

and the boundary conditions for Eq. A1 are as follows:

$$C_{NO}(z_1, t) = 0 \quad \text{(zero alveoli concentration)} \quad (A3)$$

$$\frac{dC_{NO}(z_2, t)}{dz} = 0 \quad \text{(no diffusional flux at end of airway)} \quad (A4)$$

For Eq. A3, we assume that, as z approaches zero, $C_{NO}$ approaches the constant $Ca_{NO}$. For simplicity, $Ca_{NO}$ is set to zero, as airway concentrations during a breath hold are much larger than reported values for the alveolar region $$[C_{NO}(z_1, t) \cong C_{NO}(z=0, t) = \hat{C}_{A_{NO}} = 0]$$

Consider a dimensionless form of the above governing equation. The unsteady boundary value problem of Eq. A1 is expressed in the following dimensionless form:

$$\frac{d\varphi}{d\tau} = \frac{d^2\varphi}{dx^2} - \frac{m}{x}\frac{d\varphi}{dx} - \alpha\varphi \quad (A5)$$

$$A_c = A_{c,1}x^{-m} \quad (A6)$$

where $x = \frac{z}{z_1}, \varphi = \frac{C_{NO} - Caw_{NO}}{-Caw_{NO}},$ $\tau = \frac{D_{NO,air}t}{z_1^2}, \alpha = \frac{Daw_{NO}z_1^2}{D_{NO,air}V_{air}},$ and Initial condition: $\varphi(x, \tau = 0) = 0 \quad (A7)$ Boundary condition: $\varphi(x = 0, \tau) = 1 \quad (A8)$ $$\frac{d\varphi(x_2, \tau)}{dx} = 0. \quad (A9)$$

Turn and consider the model solution. For each of the four cases (C, C-AD, T, and T-AD), the solution of the governing equation (Eq. A1) has the following form $$C_{NO} = Caw_{NO}(1-\zeta) \quad (A10)$$

where the closed form expression for $\zeta$ depends on the model as follows.

Cylinder Airway Geometry (m=0) in the Absence of Axial Diffusion (C)

$$\zeta = e^{-\alpha\tau} \quad (A11)$$

where $\alpha$ depends on $Daw_{NO}$ and is defined above.

2) Cylinder Airway Geometry (m=0) in the Presence of Axial Diffusion (C-AD)

$$\zeta = -\frac{\sinh(\sqrt{\alpha}\, x_2)}{\cosh(\sqrt{\alpha}\, x_2)} \sinh(\sqrt{\alpha}\, x) + \cosh(\sqrt{\alpha}\, x) + \sum_{n=1}^{\infty} C_n e^{-\lambda^2 \tau} x^{0.5} J_{0.5}(\gamma x) \quad (A12)$$

where, $$\gamma = \sqrt{\lambda^2 - \alpha} = \sum_{n=0}^{\infty} \frac{(n+0.5)\pi}{x_2},$$

J is the Bessel function of the first kind, and $$C_n = \frac{\int_0^{x_2}\left\{1 - \left[-\frac{\sinh(\sqrt{\alpha}\, x_2)}{\cosh(\sqrt{\alpha}\, x_2)}\sinh(\sqrt{\alpha}\, x) + \cosh(\sqrt{\alpha}\, x)\right]\right\} x^{0.5} J_{0.5}(\gamma x)\, dx}{\int_0^{x_2} x J_{0.5}^2(\gamma x)\, dx}$$

3) Trumpet Airway Geometry (m=2) in the Absence of Axial Diffusion (T)

$$\zeta = e^{-\alpha\tau} \quad (A13)$$

4) Trumpet Airway Geometry (m=2) in the Presence of Axial Diffusion (T-AD)

$$\zeta = -\frac{\cosh(\sqrt{\alpha}\, x_2)}{\sinh(\sqrt{\alpha}\, x_2)}\left[\sinh(\sqrt{\alpha}\, x) - \sqrt{\alpha}\, x\cosh(\sqrt{\alpha}\, x)\right] - \sqrt{\alpha}\, x\sinh(\sqrt{\alpha}\, x) + \cosh(\sqrt{\alpha}\, x) + \sum_{n=1}^{\infty} C_n e^{-\lambda^2 \tau} x^{1.5} J_{1.5}(\gamma x) \quad (A14)$$

where, $\gamma = \sqrt{\lambda^2 - \alpha} = \sum_{n=0}^{\infty} \frac{(n+1)\pi}{x_2}$, and $$C_n = \frac{\int_0^{x_2}\left(1 - \left\{-\frac{\cosh(\sqrt{\alpha}\, x_2)}{\sinh(\sqrt{\alpha}\, x_2)}\left[\sinh(\sqrt{\alpha}\, x) - \sqrt{\alpha}\, x\cosh(\sqrt{\alpha}\, x)\right] - \sqrt{\alpha}\, x\sinh(\sqrt{\alpha}\, x) + \cosh(\sqrt{\alpha}\, x)\right\}\right)}{\int_0^{x_2} x J_{1.5}^2(\gamma x)\, dx}$$

Figure 3B:
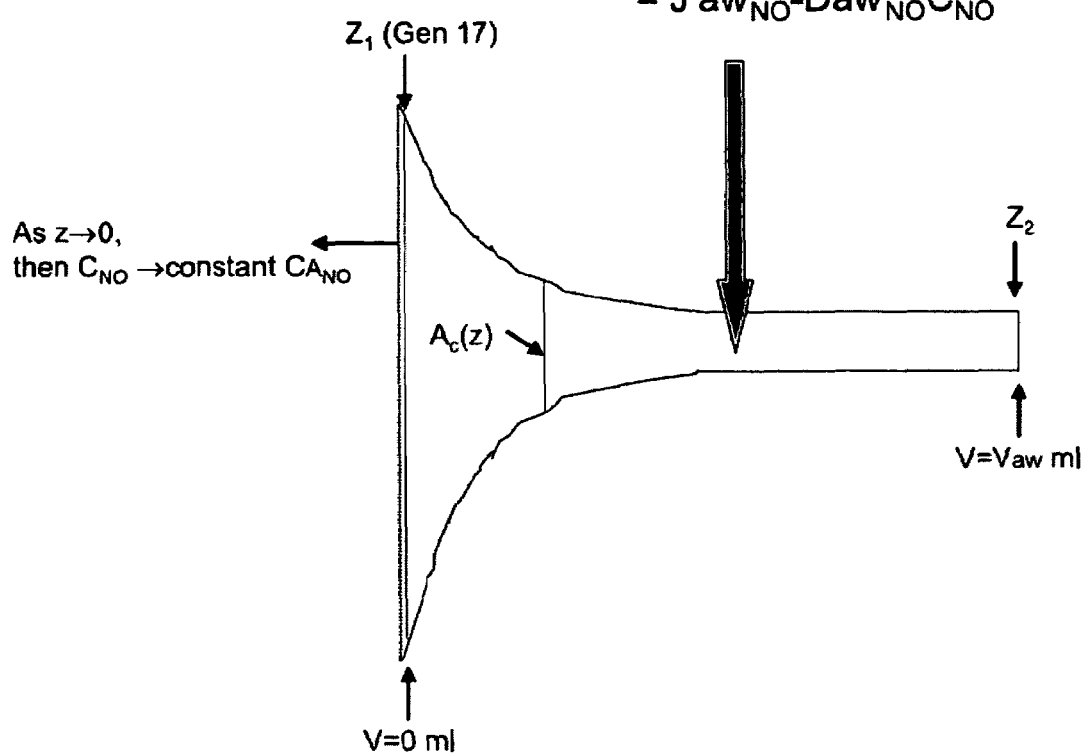
Figure 4:
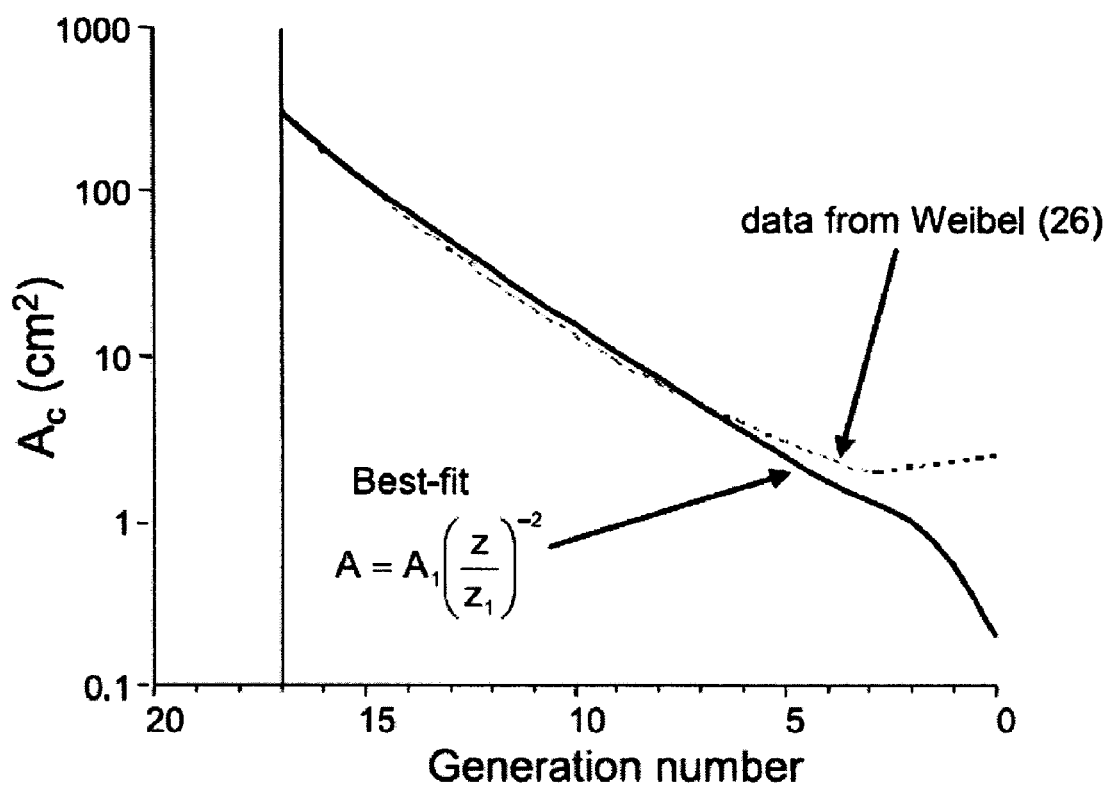
FIG. 4 is a graph of $A_c$ shown as a function of generation number. The dotted line represents the data from Weibel, and the solid line represents the best fit using the power-law relation, $A=A_1(z/z_1)^{-2}$, where $A_1$ is the cross-sectional area, and $z_1$ is the airway axial position at generation 17 (volumetric position, V, equal to 0, as shown in FIG. 2).

Consider now the trumpet model. According to Weibel's data, the cross-sectional area of the airway tree increases with distance from the mouth. Thus a more anatomically realistic model of the airway tree is a "trumpet" shape as depicted in FIG. 3B, as described previously in the prior art. The following simple relationship between airway cross sectional area ($A_c$) and axial position, z, was used to model the trumpet shape:

$$A_c = A_{c,1}\left(\frac{Z}{Z_1}\right)^{-m} \quad (1)$$

where m=2 provides an excellent match to the data of Weibel as shown in the graph of FIG. 4. Vaw and total length (i.e., $z_1$) through generation 17 was determined using the same scaling relationship described above. Generations 17-23, which include the respiratory and terminal bronchioles, and the alveoli are lumped together to become a single boundary, and $Ca_{NO}$ is set to zero. Additional details of the mathematical model are presented above.

Consider parameter estimation using different breath-hold times. Utilizing five different breath-hold times, two airway NO exchange parameters ($Daw_{NO}$ and $Caw_{NO}$) were determined for each subject and for each of the four models (i.e., C, C-AD, T, and T-AD) by matching the total mass of NO ($A_{I,II}$) accumulated in the airways during breath hold as a function of breath-hold time. Once $Daw_{NO}$ and $Caw_{NO}$ were determined, $J'aw_{NO}$ was calculated as the product $Caw_{NO} \times Daw_{NO}$. The model-predicted values of the area under the curve in phases I and II ($A^*_{I,II}$) are referenced to the experimental data, $A_{I,II}$, by minimizing the root mean square (RMS) error between the model prediction and experimental data defined by:

$$RMS = \sqrt{\sum_{i=1}^{n}(A^*_{I,II,n} - A_{I,II,n})^2/n} \quad (2)$$

where n is the number of different breath-hold times. $A^*_{I,II}$ depends on the airway NO parameters $Daw_{NO}$ and $Caw_{NO}$, as defined above, and $A_{I,II}$ for each breath-hold time was the mean of the three repeated experimental maneuvers.

Data were analyzed by using one-way and two-way repeated-measure ANOVA, followed by paired or unpaired t-tests, where appropriate, if the ANOVA analysis demonstrated statistical significance (P<0.05). All variables were assumed to be normally distributed, and all statistical tests were performed on raw data scores. A P value <0.05 was considered statistically significant. The intramaneuver and intrapopulation variability have been described in the prior art and are characterized by the 95% confidence interval expressed as a percentage of the estimated parameter value. The intramaneuver confidence interval describes the variability in a determined parameter within a single subject following the experimental protocol described above, whereas the intrapopulation confidence interval describes the anticipated range of a determined parameter within a normally distributed healthy adult population.

Figure 5A:
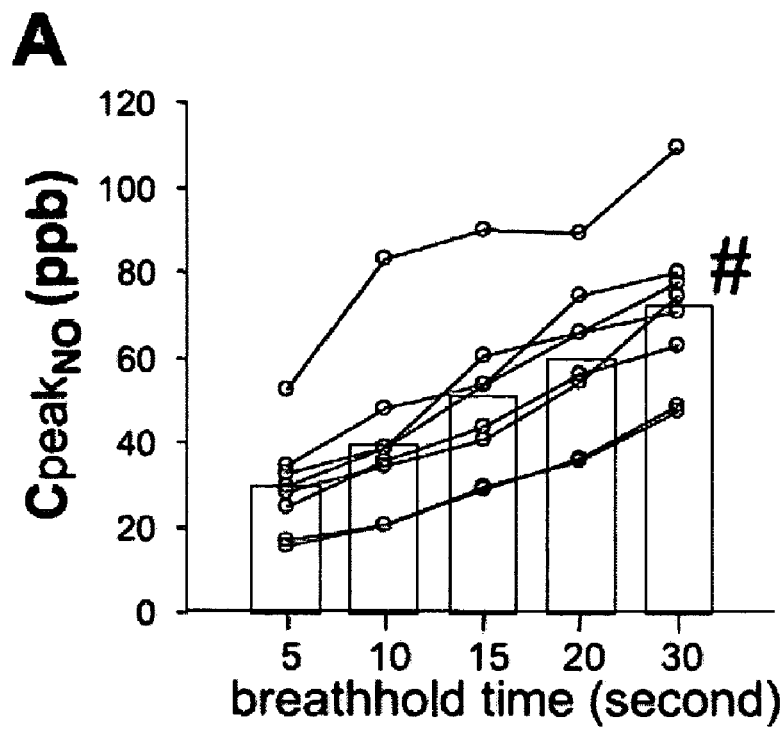
FIGS. 5a-5d are graphs of four parameters characteristic of phases I and II of the exhalation profile shown in FIG. 2, which are model independent, are presented for each of the different breath-hold times: $C_{peakNO}$ in FIG. 5s, $W_{50}$ in FIG. 5b, $V_{I,II}$ in FIG. 5c, and $A_{I,II}$ in FIG. 5d. The open circles and lines represent individual subjects, and the bars represent the mean. The sign, # denotes significant changes with breath-hold time (one-way ANOVA, $P<0.05$).
Figure 5B:
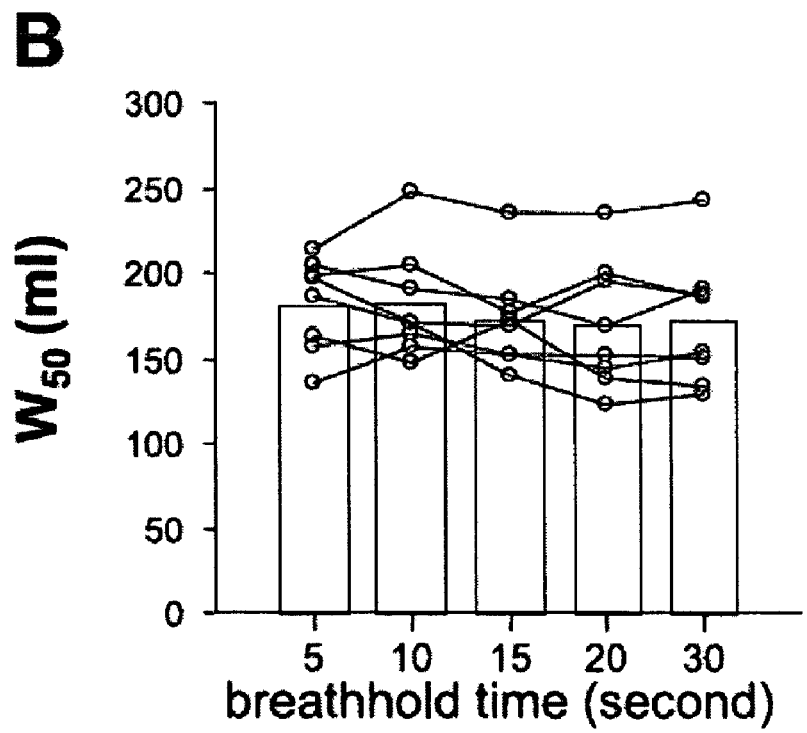
Figure 5C:
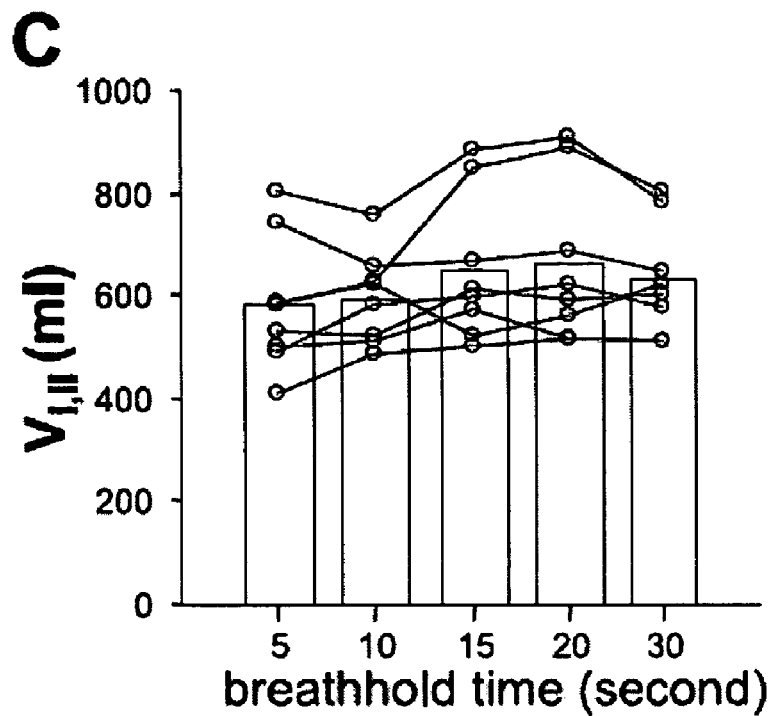
Figure 5D:
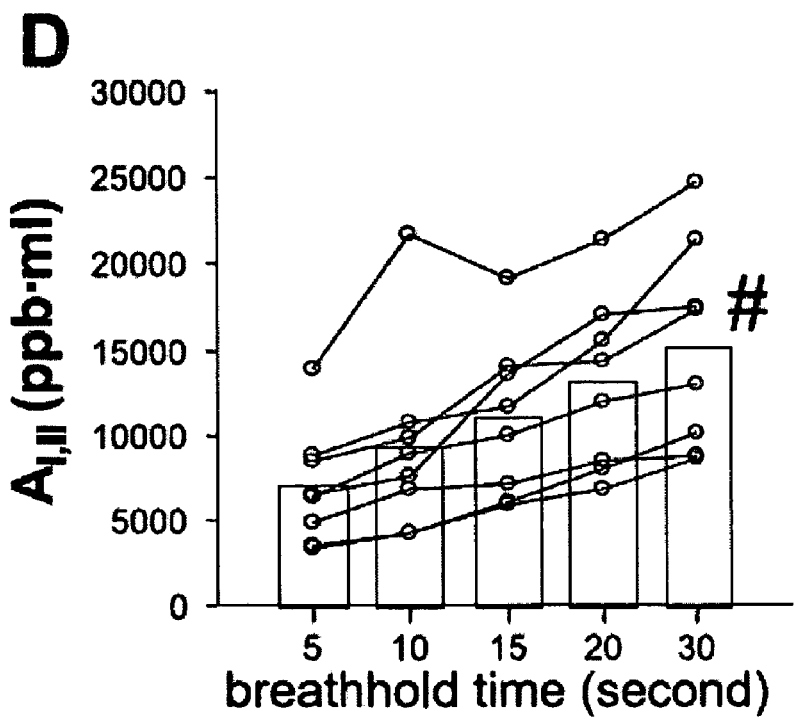

$Cpeak_{NO}$, $W_{50}$, $V_{I,II}$, and $A_{I,II}$ for all eight subjects are presented in FIGS. 5a-5d to demonstrate model-independent differences in the exhaled NO profile as a function of breath-hold time. $Cpeak_{NO}$ in FIG. 5a and $A_{I,II}$ in FIG. 4d were both a strong function of breath-hold time for all eight subjects. However, breath-hold time did not impact $W_{50}$ or $V_{I,II}$ as shown in FIGS. 5b and 5c.

The determined airway NO parameters for each of the four different models (C, C-AD, T, and T-AD) are presented in FIGS. 5a-5d. All four models can accurately simulate the increase in $A_{I,II}$ with increasing breath-hold time. The maximum deviation between $A^*_{I,II}$ and $A_{I,II}$ for any of the breathhold times are 10.0, 9.96, 10.0, and 6.00% for C, C-AD, T, and T-AD, respectively. R2 Corresponding (coefficient of determination) values are 0.94, 0.95, 0.94, and 0.98 for C, C-AD, T, and T-AD, respectively. In the absence of axial diffusion, the trumpet model (T) is identical to the cylinder model (C). In the presence of axial diffusion for the cylinder geometry (C-AD), the airway NO parameters are altered by <6% (maximum deviation is a 5.8% increase for $Caw_{NO}$). However, the impact of axial diffusion for the trumpet geometry (T-AD) is substantial. $Caw_{NO}$ and $J'aw_{NO}$ are significantly (two-way ANOVA, followed by a paired t-test, $P<0.001$ for $Caw_{NO}$ and $P<0.01$ for $J'aw_{NO}$) increased by more than 10-fold and 2-fold, respectively; $Daw_{NO}$ is significantly ($P<0.01$) decreased by about 75%. For T-AD, the mean 95% intramaneuver and intrapopulation confidence intervals for $Caw_{NO}$ and $Daw_{NO}$ are 10.5 and 11.5%, and 37.5 and 83.4%, respectively.

Figure 6A:
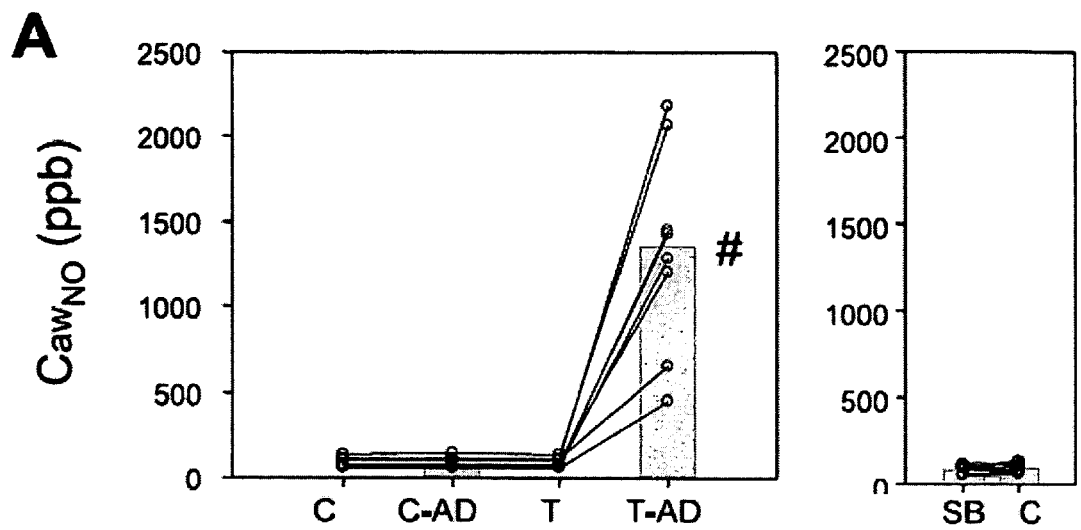
FIGS. 6a-6c on the left side are graphs showing the determined airway NO exchange parameters: $Caw_{NO}$ in FIG. 6a, $\text{Daw}_{NO}$ in FIG. 6b, and $\text{J'aw}_{NO}$ in FIG. 6c for four different cases. C is cylinder model in the absence of axial diffusion; C-AD is the cylinder model in the presence of axial diffusion; T is the trumpet model in the absence of axial diffusion; T-AD is trumpet model in the presence of axial diffusion. On the right side of FIGS. 6a-6c are the determined airway NO exchange parameters from model C, compared with the determined values from a reported single-breath technique in the prior art. The open circles and lines represent individual subjects, and the shaded bars represent the mean. The # sign denotes statistical significance among models (two-way or one-way ANOVA, P<0.05).
Figure 6B:
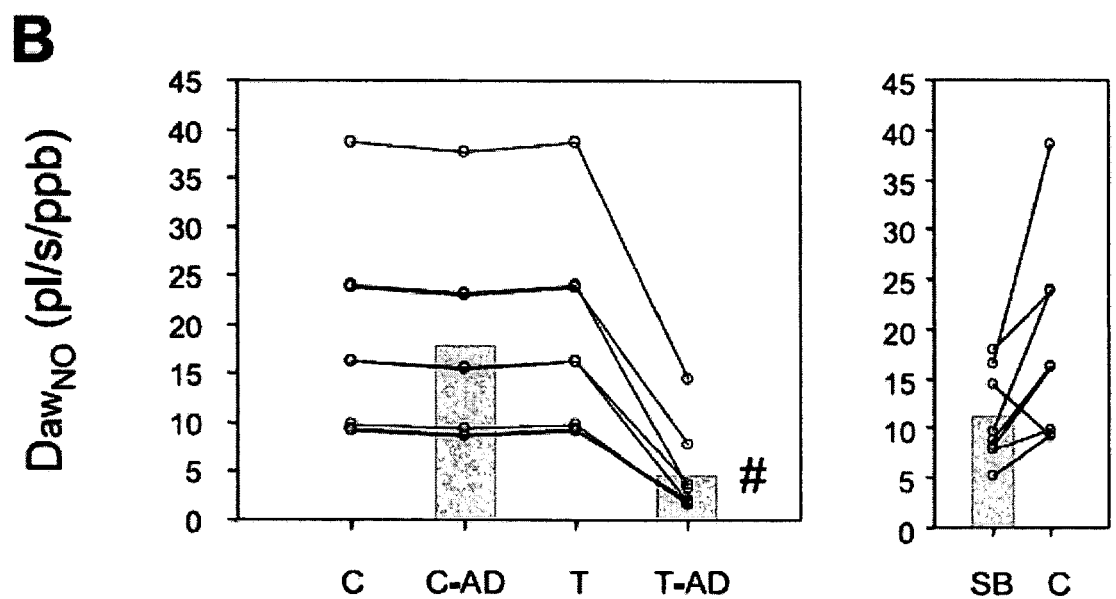
Figure 6C:
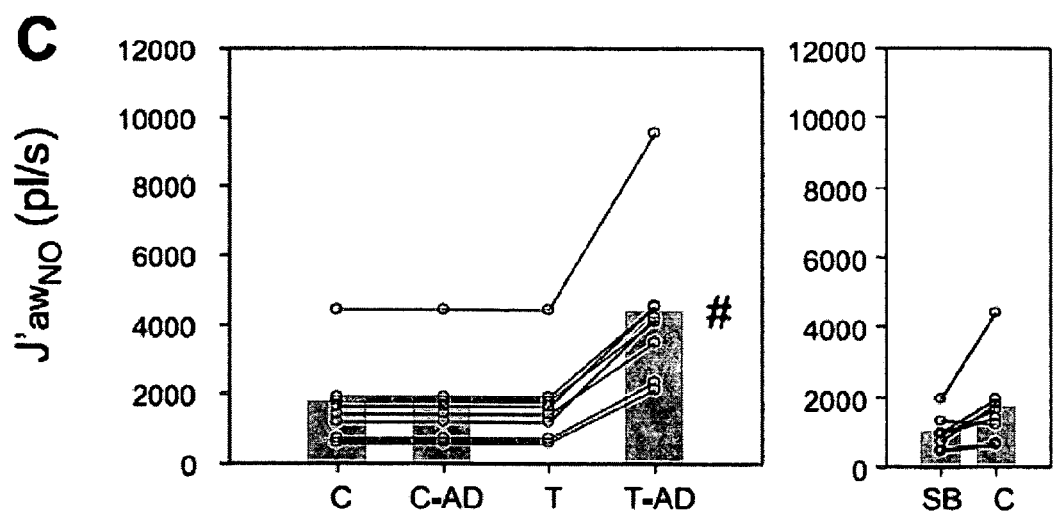

To determine the accuracy of the breath-hold technique independent of the model, the airway NO parameters from model C were compared with those obtained from the single-breath maneuver, which also utilizes model C as shown in FIGS. 6a-6c. The determined airway NO exchange parameters were not significantly different ($P<0.05$). NO concentration as a function of airway volumetric position is shown in FIG. 6a for each of the four models when breath-hold time was set to 20 s. Recall, for all four cases, that total mass of NO within the airway tree is not different, as this is the experimental variable for which the determined model parameters are chosen to match. In the absence of axial diffusion, the trumpet model (T) and cylinder model (C) predict identical and uniform (i.e., independent of volumetric position) concentration profiles. For C-AD, the concentration of NO below generation 5 begins to decrease due to loss of NO to the alveolar region. The presence of axial diffusion combined with the trumpet geometry further reduces the concentration of NO in the lower airway region, but this is compensated by a large increase in exhaled NO concentration in the gas phase of the airways (CNO) in the upper airways (above generation 12). The relative magnitude of the axial flux of NO at generation 17 ($J_{axial}$) utilizing a 20-s breath hold is presented in FIG. 7b. In the presence of axial diffusion (flux is zero in the absence of axial diffusion), the trumpet geometry increases the loss of NO to the alveolar region by 47-fold ($J_{axial}$ is 2,895 vs. 62 pl/s). At very long breath-hold times, a steady state is reached, and the loss of NO to the alveolar region in the presence of the trumpet geometry is 72-fold larger than the cylinder geometry (5,364 vs. 75 pl/s).

The sampling system has previously been shown to distort the exhaled NO by introducing a lag or delay from the mouthpiece and other valving (flag), but also a significant dispersion due to the laminar flow within the sampling line that leads to the analytical instrument. Both of these phenomena are easily accounted for, as detailed mathematically below and demonstrated in FIG. 8a.

Consider before continuing the distortion of exhaled NO concentration profile by sampling system. The experimental monitoring system continuously collects a small sampling flow ($\dot{V}_s$=4.2 ml/s) of expired air through a 1.8-mm-diameter line (volume, $V_s$=5.5 ml, and space-time, $\tau_s = \dot{V}_s N_s$=1.3 S). Since the sample line is maintained at laminar flow, the resulting concentration input to the NO analyzer, $C_{inNO}(t)$, is delayed and distorted, and this effect can be approximated in terms of a convolution integral:

$$t \leq \tau_s/2 : C_{in_{NO}}(t) = 0 \tag{B1}$$

$$t > \tau_s/2 : C_{in_{NO}}(t) = (\tau_s^2/2) \int_0^{t-\tau_s/2} \frac{C_{sNO}(u)}{(t-u)^3} du \tag{B2}$$

where $C_{sNO}(t)$ is the NO concentration at the sampling point.

In addition, before exhaled air from the mouth (concentration, $Ce_{NO}$) is sampled, it traverses a dead space region (characterized by plug flow) within the mouthpiece assembly (volume, $V_{ds}$=135 ml). Thus the concentration entering the sampling line, CsNO, is delayed by space-time, $\tau_{ds} = V_{ds}/\dot{V}_E$, relative to $Ce_{NO}$, or $CsNO(t) = Ce_{NO}(t-\tau_{ds})$. $\dot{V}_E$ represents exhalation flow rate (ml/s). Although the analyzer's response may also be characterized by a convolution integral, the instrument imparts minimal distortion on the signal; thus the instrument response is modeled as a brief additional lag of 0.15 s. Thus numerical integration of $CsNO(t) = Ce_{NO}(t-\tau_{ds})$ using Eqs. B1 and B2 yields $C_{inNO}(t)$, which is translated in time to obtain the observed NO concentration from the instrument, $C_{obsNO}(t)$.

Figure 7A:
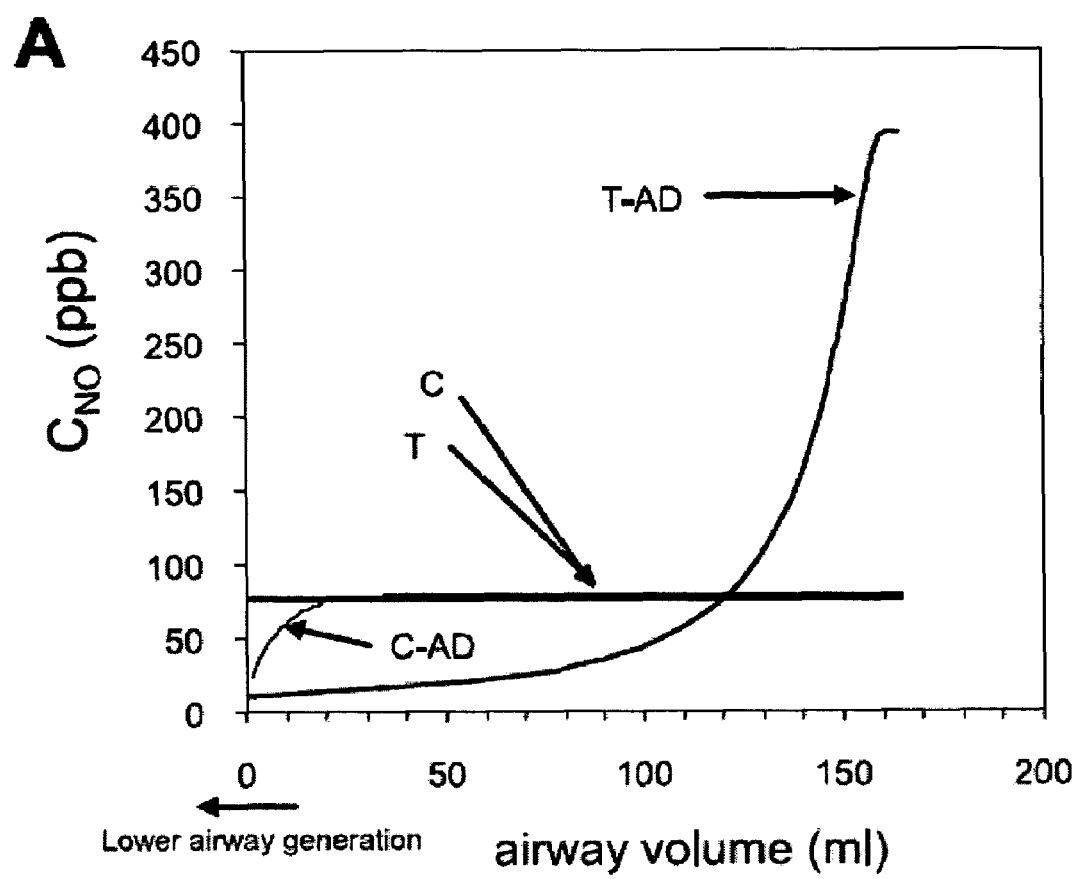
FIG. 7a is a graph showing $C_{NO}$ as a function of volumetric position in the airway tree is shown for four cases: C, C-AD, T, and T-AD.
Figure 8A:
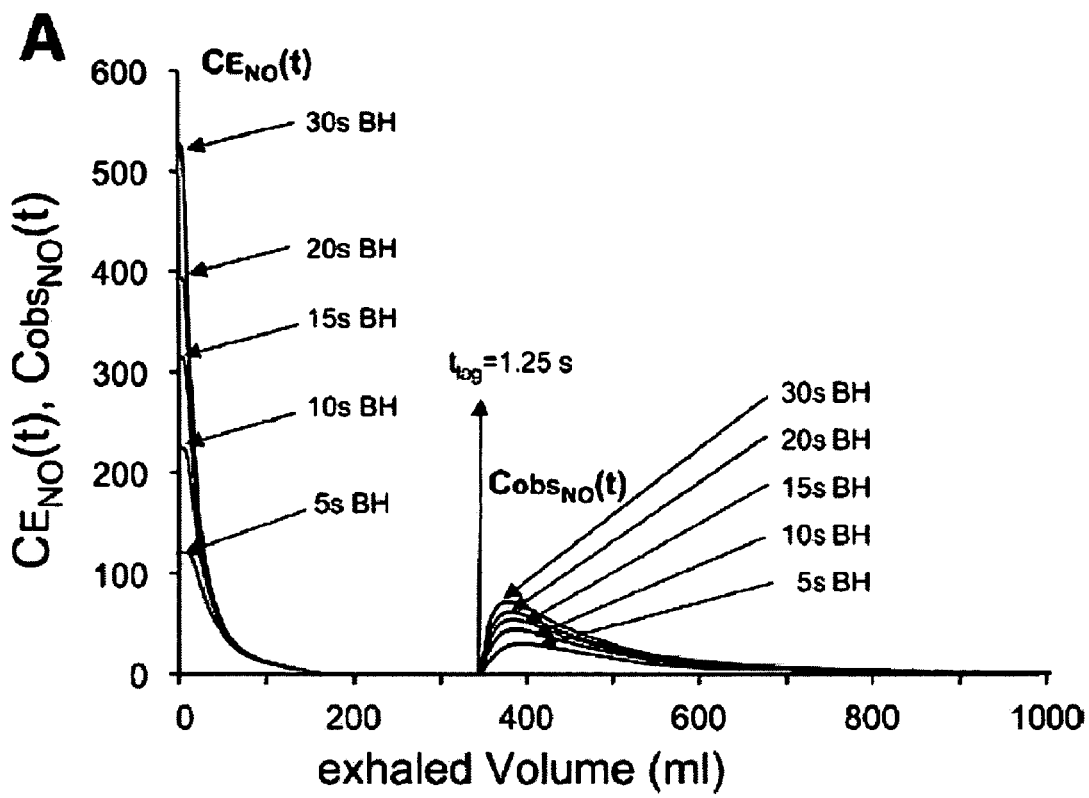
FIG. 8a is a graph using the mean value for the best-fit airway NO parameters ($\text{Daw}_{NO}$=4.5 pl s$^{-1}$ ppb$^{-1}$, $\text{Caw}_{NO}$=1,340 ppb), the exhaled concentration at the mouth ($\text{Ce}_{NO}$; before entering the sampling system) is shown for a series of breath-hold (BH) times. The shape of this profile exactly replicates the NO concentration profile with volumetric position in the airway tree at the end of the breath hold. $\text{Ce}_{NO}$ then enters the sampling system, which introduces a time lag ($t_{lag}$=1.25 s) as well as a significant flattening and broadening of the peak due to dispersion within the laminar flow of the sampling line to the analytical instrument. The result is the observed concentration profile, $C_{obsNO}$, by the instrument.
Figure 8B:
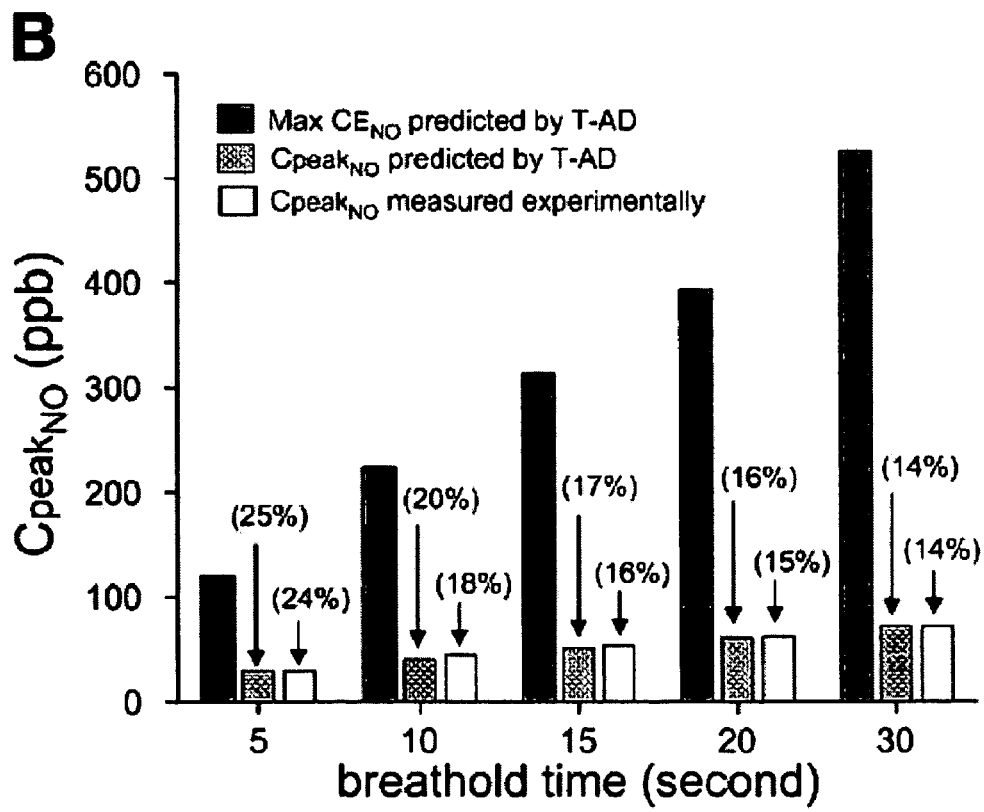
FIG. 8b is a graph maximum NO concentrations in the exhaled profile are shown for three cases at each of the different breath-hold times. Dark shaded bar represents the calculated maximum $\text{Ce}_{NO}$ concentration from the model simulation in FIG. 8a; light shaded bar represents the calculated maximum $C_{obsNO}$ ($C_{peakNO}$) from the model simulation in FIG. 8a; and the open bar represents $C_{peakNO}$ from the experimental observation. $C_{peakNO}$ as a fraction of the maximum $\text{Ce}_{NO}$ are shown as percentages in parentheses.

In this simulation, the model-determined airway NO parameters (mean for all eight subjects) for T-AD are used to simulate breath-hold times from 5 to 30 s. The NO concentration profile in the airway tree then exits the mouth (CENO) and enters the sampling system. Note the similarity in shape of this profile (FIG. 8a) for a 20-s breath hold to that presented in FIG. 7a. The sampling system then introduces a lag ($t_{lag}$<1.25 s for an exhalation flow of 300 ml/s) and also significantly flattens and broadens the shape of the profile observed by the instrument, denoted $C_{obsNO}(t)$ due to dispersion in the sampling line as shown in FIG. 8a. The total mass of NO exhaled from the airway tree is not changed, but $C_{peakNO}$ is reduced to 14-25% of the maximum concentration within the airway tree, depending on the breath-hold time. $C_{obsNO}(t)$ predicted by the model (light shaded bars, FIG. 8b) agrees well with that observed experimentally (open bars).

The illustrated embodiment thus presents a new method utilizing a series of different breath-hold times to characterize airway NO exchange using three parameters ($Caw_{NO}$, $Daw_{NO}$, and $J'aw_{NO}$). The parameters can be determined by matching a model to experimentally observed values of the total mass of NO exhaled from the airway following a breath hold. Four different model cases explored the impact of both axial diffusion of NO in the gas phase and airway geometry. The results demonstrate two major findings. First, the NO parameters from the new technique are not different from values of a previously described single-breath technique using a cylinder geometry in the absence of axial diffusion. Second, $Caw_{NO}$ is more than 14-fold higher when axial diffusion and a trumpet-shaped airway geometry are considered. Thus we conclude that our new breath-hold technique has the potential to characterize airway NO exchange and that previous model simplifications regarding transport mechanisms (i.e., neglecting axial diffusion) and airway geometry (i.e., simple cylinder) have profound implications in the interpretation of airway NO exchange mechanisms. The latter emphasizes the importance of considering axial diffusion and the trumpet shape of the airway tree in models that seek to describe endogenous NO production and elimination.

Consider the efficacy of breath-hold technique. Relative to prior art single-breath techniques, the breath-hold technique of the illustrated embodiment has two distinct advantages. First, the exhalation flow need not be controlled, providing a simpler maneuver to complete for both the subject and the investigator or clinician. Second, the technique provides improved accuracy (smaller confidence interval) for estimating $Daw_{NO}$ relative to the single-breath technique with a 20-s breath hold and decreasing exhalation flow. The intramaneuver confidence interval for the single-breath technique is 168%, compared with 11.5% for the breath-hold technique of the illustrated embodiment.

The improved confidence interval is due to two factors. First, the new breath-hold technique requires more individual breathing maneuvers (five breath-hold times) than the single-breath technique (one maneuver); however, each maneuver may be easier to complete for both the subject and the investigator. Second, the new technique samples a wider range of residence times (5-30 s) within the airway tree compared with the single-breath technique (20 s only). A disadvantage of the new technique is the inability to characterize the alveolar region, simply because air originating from this space is not sampled.

Finally, to preserve simplicity, the technique of the illustrated embodiment considers only the total mass of NO exhaled in phases I and II and does not analyze phase III. The scope of the invention includes a more detailed analysis of the precise shape of the exhalation NO profile in phases I and II. For example, analysis of the width or skewness of the phase I and II peak might provide more detailed information on the location of NO production within the airway tree, which could be relevant in disease states such as asthma. In addition, our current estimates of $Daw_{NO}$ and $Caw_{NO}$ are averages over the entire airway tree and do not account for dependence on transport properties of surrounding tissue (e.g., tissue thickness), which may vary with axial position.

Figure 7B:
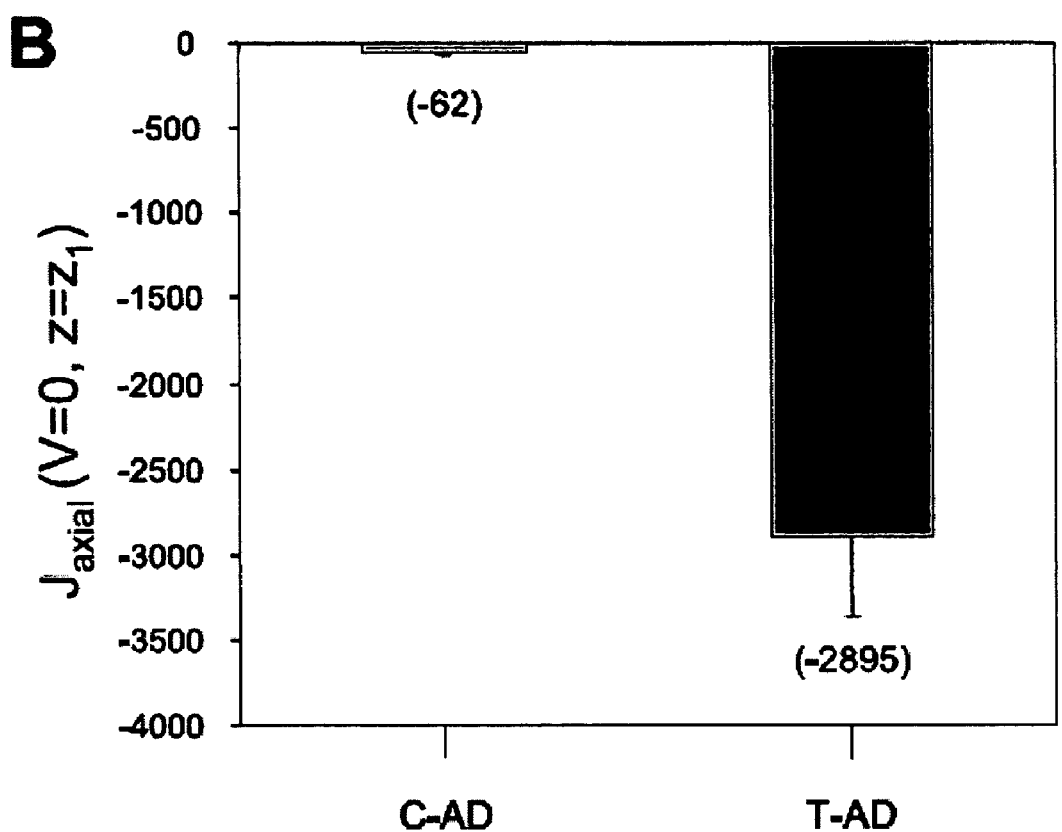
FIG. 7b is a graph of the axial flux of NO from diffusion ($J_{axial}$) at generation 17 based on Fick's first law of diffusion is shown for both C-AD and T-AD. The significant difference is due to increased cross-sectional area at generation 17 in the trumpet shape shown in FIG. 3b.

Axial diffusion is a fundamental mode of transport for gases in the lungs, and its relative importance depends on the competing mechanisms of transport, namely forced convection (or bulk fluid flow). The relative importance of axial diffusion increases with position into the airway tree due to the branching structure of the airway tree and thus a decreasing bulk fluid flow rate within an individual airway. Recent theoretical and experimental studies clearly demonstrate that axial diffusion has a significant impact on the exhaled NO signal and thus the characterization of NO exchange dynamics. By comparing different airway geometries in the presence and absence of axial diffusion, it is evident that axial diffusion results in a significant loss of NO to the alveolar region for the trumpet-shaped airway. This tremendous increase relative to the cylinder geometry as shown in FIG. 7b is due to the substantial increase in the cross-sectional area available for diffusion in the small airways (283 cm² compared with 6 cm² at generation 17. Thus, to simulate the experimentally observed total mass of NO accumulated in the airways during breath hold, the model must increase the $J'aw_{NO}$ to offset the loss to the alveolar region.

To increase the airway wall flux to compensate for losses to the alveolar region, the model can either increase the conductance (i.e., increase $Daw_{NO}$), increase the concentration difference between the airway wall and the gas phase in the airway lumen (i.e., increase $Caw_{NO}$), or some combination of both. This is described mathematically above in Eq. A1. These options can be uniquely distinguished from each other by using the breath-hold technique. During a breath hold, NO accumulates in the gas phase, thus increasing the concentration. The final (or steady-state) concentration is determined by $Caw_{NO}$, and the rate at which the concentration changes is determined by $Daw_{NO}$.

Figure 9:
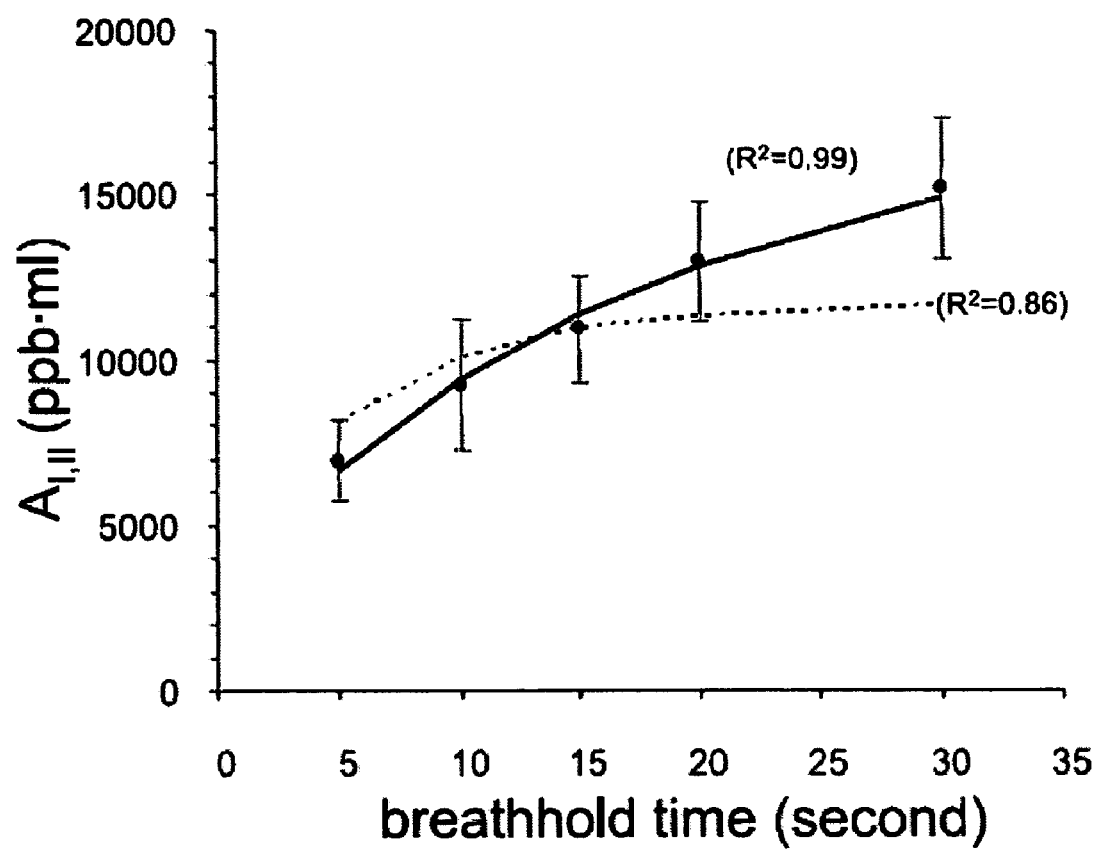
FIG. 9 is a graph of mean values of the eight healthy subjects for $A_{I,II}$ are shown as a function of breath-hold time (solid circles). The error bars represent the SD. The solid line is the best fit of these data points ($R^2$=0.99) using the model with a trumpet-shaped airway geometry and considering axial diffusion (T-AD) when both $\text{Daw}_{NO}$ and $\text{Caw}_{NO}$ are adjusted. Best-fit values for parameters $\text{Daw}_{NO}$ and $\text{Caw}_{NO}$ are 2.69 pl s$^{-1}$ ppb$^{-1}$ and 1,603 ppb, respectively ($\text{J'aw}_{NO}$=$\text{Daw}_{NO}\times\text{Caw}_{NO}$=4,312 pl/s). The dashed line represents the best fit for the T-AD model when $\text{Daw}_{NO}$ is held constant at the best value (18.4 pl s$^{-1}$ ppb$^{-1}$) when the cylinder-shaped airway model is used and axial diffusion is neglected, and then only $\text{Caw}_{NO}$ is adjusted to determine the best fit. In this case, the best value for $\text{Caw}_{NO}$ is 335 ppb, but the overall fit of the data is significantly worse ($R^2$=0.86), demonstrating the need to adjust both parameters to achieve the best fit of the data.

FIG. 9 demonstrates why both $Caw_{NO}$ and $Daw_{NO}$ must both be changed to simulate the experimental observations. The dotted line demonstrates the best fit of the average $A_{I,II}$ as a function of breath-hold time for all eight subjects when $Daw_{NO}$ is held constant at the best value when axial diffusion is neglected, and only $Caw_{NO}$ is increased to increase the airway wall flux when axial diffusion is considered. Note that the mass of NO in the airway rises too quickly (too large of a conductance) to a steady-state value that is too small. Any further increases in CawNO to match the experimental observations at higher breath-hold times result in a poorer match at shorter breath-hold times. Thus, to match the experimental observations, both an increase in $Caw_{NO}$ and a decrease in $Daw_{NO}$ (smaller conductance) are necessary. In the presence of axial diffusion and a trumpet-shaped airway geometry, the predicted increase in the maximum airway wall flux ($J'aw_{NO}=Caw_{NO} \times Daw_{NO}$) is 2.6-fold (4,346 compared with 1,704 pl/s), which is consistent with previous reports that utilized models that considered axial diffusion and reported increases in $J'aw_{NO}$ that ranged from 1.5- to 5-fold. The major difference in our current simulations is the ability to more accurately separate the terms that comprise $J'aw_{NO}$ (i.e., $Caw_{NO}$ and $Daw_{NO}$). The result is a mean $Caw_{NO}>1.3$ ppm, which is more than 14-fold higher than current (mean 91 ppb) and previous estimates (range 75-225 ppb) from models that neglect axial diffusion.

Others in the art have employed an experimental approach and calculated the gas-phase equilibrium NO concentrations in different regions of the airway tree, which are equivalent to $Caw_{NO}$. Their results are based on a model that is identical to the current model T; that is, the model is based on a trumpet-shaped geometry to determine volumetric positions and total airway volume and neglects axial diffusion. Thus the technique utilizes a simple exponential solution for the time dependence of the gas-phase concentration in the airways during a breath hold, which is equivalent to Eq. A13. Based on a fit through two data points (e.g., 0- and 10-s breath hold), they report equilibrium (or $Caw_{NO}$) concentrations that range from 16 to 56 ppb in healthy young adults from the respiratory bronchioles to the trachea, which are consistent with our reported $Caw_{NO}$ using model T. The reported lower concentrations in the lower airways found in prior art research may be due to increased loss of NO to the alveolar region by axial diffusion.

This much larger wall concentration has potentially important implications for physiological processes in the airway wall, which are concentration dependent, such as the activation of soluble guanylate cyclase, which has recently been shown to be activated at concentrations as low as 3 ppm (about 5 nM). Thus, in asthma, where exhaled NO concentrations can be increased more than fivefold, $Caw_{NO}$ values may reach levels that impact airway and vascular smooth muscle tone.

Consider gas phase relative to tissue-phase concentration. During a breath hold, the concentration of NO in the airways increases because the concentration in the tissue phase (i.e., wall concentration, $Caw_{NO}$) is larger than that in the gas phase. For a very long breath-hold time, the gas-phase concentration, $C_{NO}$, would eventually reach $Caw_{NO}$. Our estimated mean $Caw_{NO}$ is 1,340 ppb, which is much larger than the experimentally observed peak concentration of 71 ppb following the largest breath-hold time of 30 s.

This discrepancy is due to two phenomena. First, the sampling system introduces significant distortion of the observed exhaled profile due to axial dispersion of the gas within the sampling line leading to the NO analyzer. This causes a pulse of NO to be significantly flattened (thus lowering the peak concentration) and broadened without altering the total mass of NO in the peak. This effect can be accurately simulated using a well-studied and validated convolution for laminar flow in a tube, as described above. The result is a four- to sevenfold reduction in maximum or peak concentration. For the 30-s breath hold, the T-AD model predicts a maximum concentration of 526 ppb within the airways, but a $C_{peakNO}$ (observed at the instrument) of only 72 ppb, which agrees very well with the experimentally observed value of 71 ppb.

The second reason why the observed gas concentration is less than $Caw_{NO}$ is due to the observation that a steady state has not been reached with the gas phase. In other words, the gas phase is not at equilibrium with the tissue phase. This can be observed by simply noting that $C_{peakNO}$ following a 30-s breath-hold time is significantly larger than that following the 20-s breath-hold time. The question is: how long does it take for the gas phase to reach equilibrium with the tissue phase? This can be estimated from the T-AD model and determining the time is takes to reach 95% of the final equilibrium concentration (i.e., $Caw_{NO}$). This time (mean±SD) to equilibrium is 226±168 s (3.75 min) for the eight healthy subjects.

The illustrated embodiment is a method and apparatus in which the method may be performed based on progressively increasing breath-hold times to characterize airway NO exchange. The technique is relatively simple to perform and does not require monitoring or control of exhalation flow, and determined airway NO parameters agree well with a previously described single-breath technique. In addition, the impact of two important physical and anatomical features, neglected for simplicity in previous models, have been included; namely, axial diffusion of NO in the gas phase and an increasing cross-sectional area of the airway tree with axial position (i.e., trumpet shape). In the presence of axial diffusion and a trumpet shape, the model predicts a significant back diffusion of NO from the airways into the alveolar region, which profoundly impacts the determination of airway NO parameters. In particular, the wall concentration of NO in healthy adults is more than an order of magnitude larger than previous estimates. This concentration (>1,300 ppb) approaches that capable of activating soluble guanylate cyclase and thus smooth muscle relaxation, particularly in disease states such as asthma. We conclude that the breath-hold technique of the illustrated embodiment may have potential to characterize airway NO exchange in subjects unable to perform single-breath exhalations. In addition, accurate characterization of airway NO exchange should include mathematical models, which consider axial diffusion of NO in the gas phase as well as the trumpet shape of the airway tree.

Turning now to an examination of axial diffusion of NO in the lungs using heliox and air, we have developed a methodology that focuses on the determination of the airway wall NO parameters ($Caw_{NO}$, $Daw_{NO}$, and $J'aw_{NO}$). The methodology uses a series of different breath-holding times that significantly improves the accuracy of determining $Daw_{NO}$ and suggests that, indeed, the estimation of $Daw_{NO}$ also depends on axial diffusion and airway geometry. The object is to alter the rate of axial molecular diffusion of NO in the gas phase of the airway tree by using heliox (80% helium, 20% oxygen) as the insufflating gas and then accurately estimate airway wall NO parameters using the above described breath-holding technique. Because the airway NO parameters characterize features of the airway wall or tissue, such as airway wall surface area, tissue thickness, and net rate of tissue production, they should be independent of the physical properties of the insulating gas. To investigate this premise, our model of NO exchange must capture the relevant physical properties of the insufflating gas (e.g., rate of molecular diffusion), including the space it occupies (e.g., airway geometry).

The experimental method was again applied to nine healthy adults (age 21-38 yr, five female) participated in the study as shown in Table 2. All subjects had a ratio of forced expiratory volume in 1 s to forced vital capacity ($FEV_1/FVC$) of >0.75 at the time of testing. In addition, all subjects had no history of smoking at any time and no history of cardiovascular, pulmonary, or neurological diseases.

The protocol used was that disclosed above, namely, each subject performed a series of breath-hold maneuvers (5-, 10-, 15-, 20-, and 30-s breath hold) using either air or heliox as the insufflating gas during inspiration from functional residual capacity to total lung capacity. We have previously demonstrated that a tidal breathing wash-in period of heliox for 2 min before the inspiration of heliox and the breath hold does not significantly impact exhaled NO concentration and thus was not included in the present protocol. The presence of heliox increases the molecular diffusivity of NO in the gas phase from 0.23 to 0.52 $cm^2/s$ relative to air. Exhalation flow after a breath hold was not controlled but was generally >200 ml/s to ensure evacuation of the airway space in about 2 s. A positive pressure >5 cmH2O was maintained during the breath hold and exhalation to prevent nasal contamination. A schematic of the experimental apparatus again is shown in FIG. 1. After indexes of NO exchange dynamics were measured, general spirometry including FVC and $FEV_1$ were measured in all subjects (Vmax229; Sensormedics, Yorba Linda, Calif.) by using the best performance as summarized in Table 2 from three consecutive maneuvers.

Consider now an airstream analysis. A chemiluminescence NO analyzer (NOA280, Sievers, Boulder, Colo.) was used to measure the exhaled NO concentration. The instrument was calibrated on a daily basis using a certified NO gas (45 ppm NO in 100% N2 for air calibration and 45 ppm NO in 100% He for heliox calibration, Sievers). The zero-point calibration was performed with an NO filter (Sievers) immediately before the collection of a profile. Calibration with ≧80% of carrier gas (either nitrogen or helium as in the case of air or heliox, respectively) balanced with oxygen resulted in a negligible change in the response of the instrument (<2% for helium). The flow rate and pressure signals were measured by using a pneumotachometer (RSS100HR, Hans Rudolph, Kansas City, Mo.). The pneumotachometer was calibrated before each subject and set to provide the flow in units of STPD and pressure in units of cm $H_2O$. The software of the pneumotachometer accounts for changes in gas properties (e.g., viscosity) when using heliox as the insufflating gas.

Consider the empirical data analysis. Experimental exhalation profiles after breath hold from air and heliox breathing were characterized empirically independent of a mathematical model or "model independent" by the peak or maximum observed concentration in phase I and II as is also diagrammatically depicted in FIG. 3b of the above methodology illustrating the exhalation profile, $C_{NO}$ peak; the width of phase I and II, $W_{50}$, defined as the exhaled volume in which the NO concentration was greater than 50% of $C_{NO}$ peak; $V_{I,II}$, the total exhaled volume of phase I and II; and $A_{I,II}$ the total mass or volume of NO (area under the curve) in phase I and II.

The data is again modeled and simulated using a trumpet model. Mathematical models to estimate airway wall NO parameters in this embodiment were developed for two cases: 1) trumpet airway in the absence of axial diffusion (T), and 2) trumpet airway in the presence of axial diffusion (T-AD). Details of these models, including the derivation of the governing equations and solutions, are disclosed above, and only the salient features which illustrate the additional embodiment will be described.

For each subject as before, airway geometry was characterized by appropriately scaling the lengths and diameters of Weibel's data of the human airway tree, on the basis of the conducting airway volume (Vaw) of generations 0-17 of each subject. The trumpet shape of the airway is shown in FIG. 3b, and was captured using the following relationship between airway cross-sectional area ($A_c$) and axial position, z as shown in equation A2 above, where the exponent m=2 provides an excellent match to the data of Weibel. The remaining generations (generations 18-23), including the respiratory and terminal bronchioles and the alveoli, are lumped together and assumed to be at $Ca_{NO}$. Because reported values of CANO are generally <2 parts per billion (ppb), much lower than those observed in the airway tree during the breath-hold times of the present technique, $Ca_{NO}$ was set to zero as one of the boundary conditions.

Turn to parameter estimation using different breath-hold times. As before, utilizing five different breath-hold times, two model-dependent, airway wall NO exchange parameters ($Daw_{NO}$ and $Caw_{NO}$) from the two different models (i.e., T and T-AD) were uniquely determined for each subject by matching the total mass of NO ($A_{I,II}$) accumulated in the airway gas phase during breath hold as a function of breath-hold time. The model-predicted values of the area under the curve in phase I and II, $A^*_{I,II}$, are referenced to the experimental data, $A_{I,II}$, by minimizing the root mean square error between the model prediction and experimental data. On the basis of the governing equations of the model, $A^*_{I,II}$ depends on the airway wall NO parameters $Daw_{NO}$ and $Caw_{NO}$. Once $Daw_{NO}$ and $Caw_{NO}$ were determined, $J'aw_{NO}$ was calculated as the product of $Caw_{NO}$ and $Daw_{NO}$.

As before data were analyzed by one-way and two-way repeated-measures ANOVA, followed by paired or unpaired t-tests as appropriate, if the ANOVA analysis demonstrated statistical significance (P<0.05). All variables were assumed to be normally distributed, and all statistical tests were performed on raw data scores. Outliers were defined by raw values that exceed three standard deviations from the mean. A P value <0.05 was considered statistically significant.

Figure 10A:
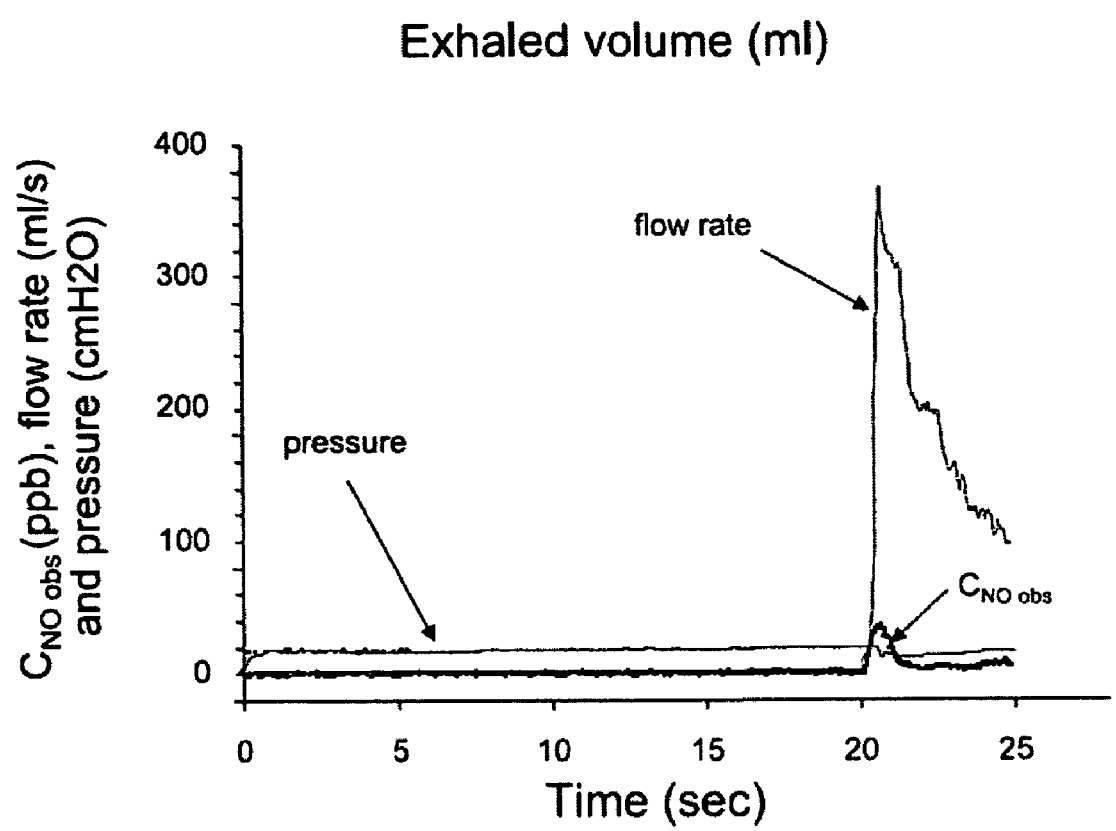
FIG. 10a is a graph of representative experimental exhaled profile after 20-s breath hold to present NO, flow rate, and pressure tracing.
Figure 10B:
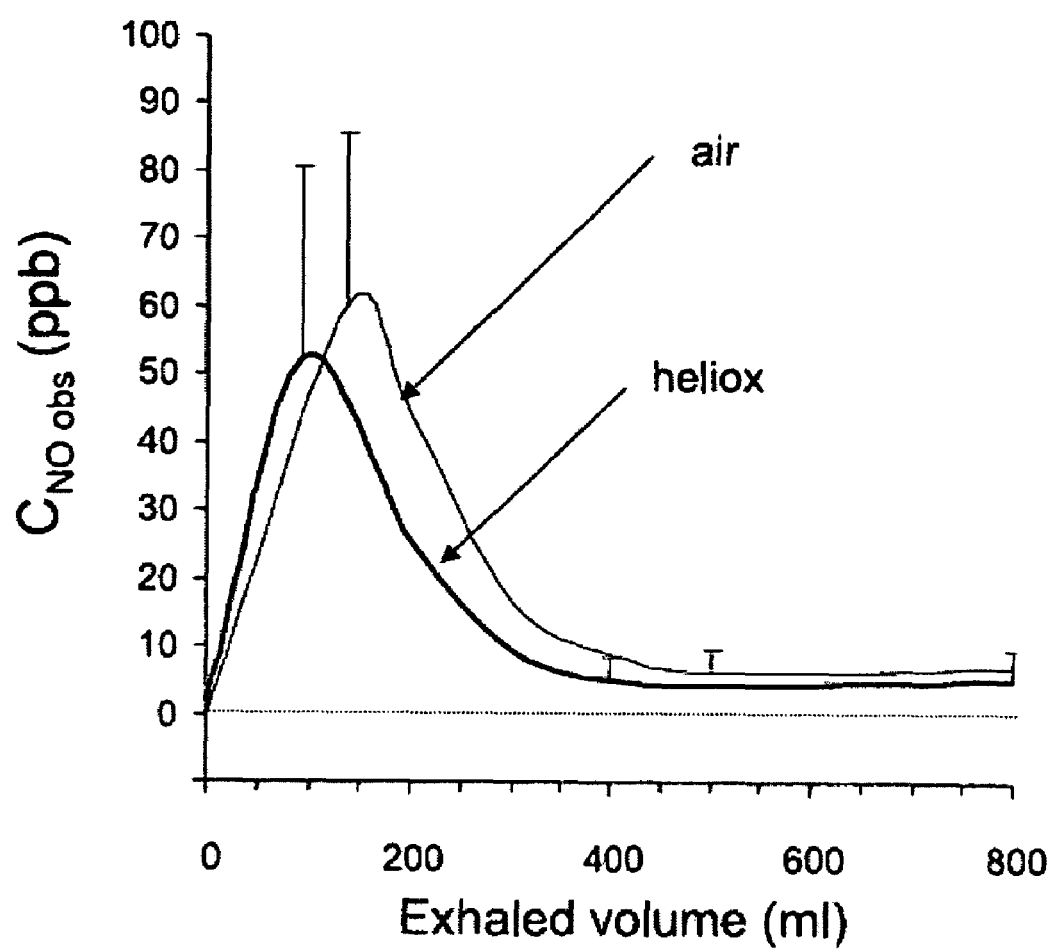
FIG. 10b is a graph of the composite or mean of the nine healthy subjects, experimental NO exhalation profile (error bars are standard deviation) is presented for 20-s breath-hold maneuver for air and for heliox.
Figure 11A:
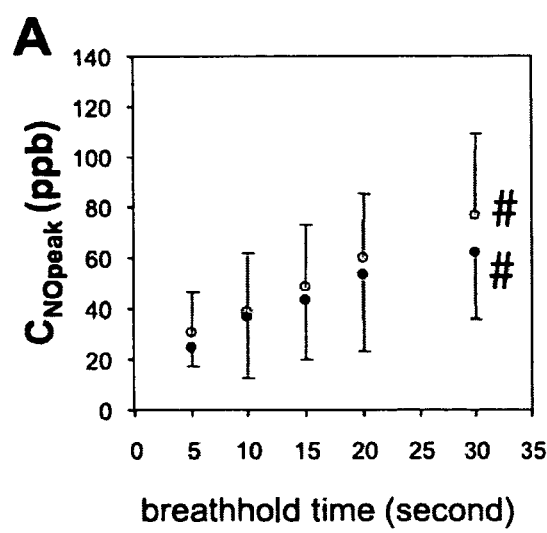
FIGS. 11a-11d are graphs illustrating four parameters characteristic of phase I and II of the exhalation profile in FIG. 2 that are model independent are presented for each of the different breath-hold times: $C_{NO\ peak}$ is shown in FIG. 11a, $W_{50}$ is shown in FIG. 11b, $V_{I,II}$ is shown in FIG. 11c, and $A_{I,II}$ is shown in FIG. 11d. Open circles with lines represent the mean and standard deviation from air breathing, and solid circles with lines represent the mean and standard deviation from heliox breathing. The pound sign # denotes statistically significant changes with breath-hold time (1-way ANOVA, P<0.05). The askterik * denotes statistically significant difference between air and heliox breathing (paired t-test, P<0.05).
Figure 11B:
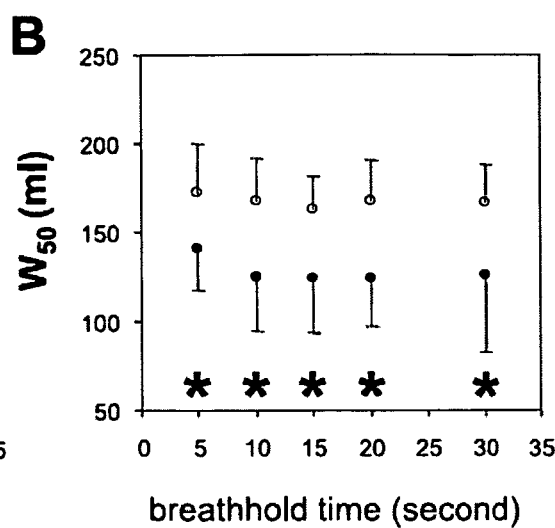
Figure 11C:
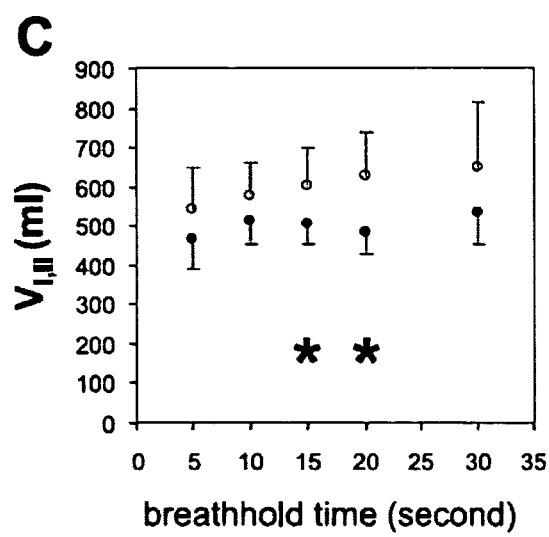
Figure 11D:
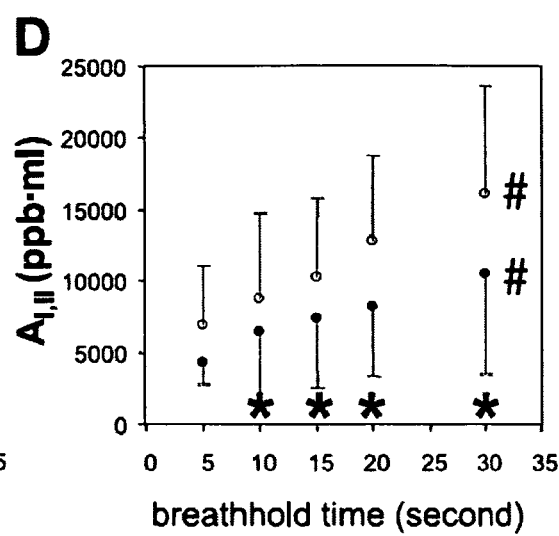

FIG. 10a presents a representative single tracing for the exhaled NO concentration profile as observed by the analytical instrument ($C_{NO\ obs}$), exhalation flow, and pressure for inspiration of air using 20-s breath-hold time. FIG. 10b presents the representative composite (average of all subjects) $C_{NO\ obs}$ for air and heliox using a 20-s breath-hold time. The composite profile was attained by taking the mean exhaled concentration at equivalent exhaled volume intervals in the nine healthy subjects. A decrease in total mass of NO exhaled in phases I and II ($A_{I,II}$) was observed when heliox was used as the insufflating gas (36% reduction in heliox breathing), although $C_{NO}$ peak was not statistically lower.

$C_{NO}$ peak, $W_{50}$, $V_{I,II}$, and $A_{I,II}$ for all nine subjects are presented in FIGS. 11a-11d to demonstrate model-independent differences in the exhaled NO profile as a function of breathhold time as well as the differences between air and heliox breathing. For both air and heliox breathing, $C_{NO}$ peak in FIG. 11a and $A_{I,II}$ in FIG. 11d were both strong positive functions of breath-hold times for all nine subjects. However, breathhold time did not impact $W_{50}$ or $V_{I,II}$ in FIGS. 11b and 11c. $C_{NO}$ peak did not depend on the presence of heliox; however, $W_{50}$ and $A_{I,II}$ (except 5-s breath hold) were all significantly reduced in the presence of heliox, independent of breath-hold times. $V_{I,II}$ tended to be lower in the presence of heliox but only reached statistical significance for breathhold times of 15 and 20 s.

Figure 12A:
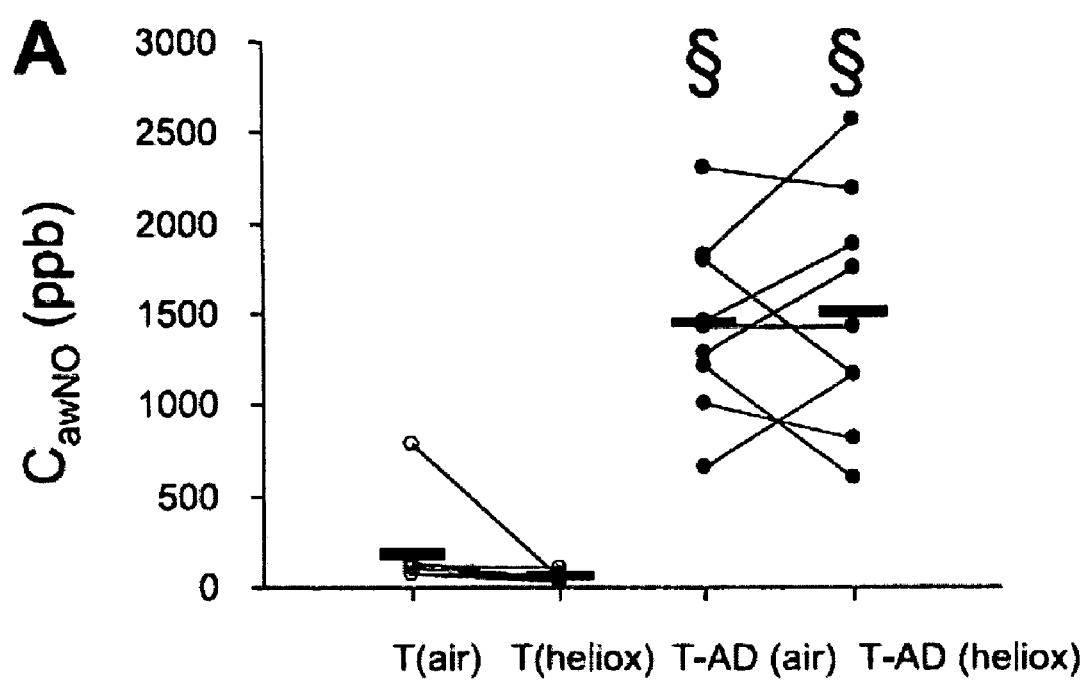
FIGS. 12a-12c are graphs which illustrate the determined airway wall NO exchange parameters from a trumpet shaped airway: $\text{Caw}_{NO}$ is illustrated in FIG. 12a, $\text{Daw}_{NO}$ is illustrated in FIG. 12b, and $\text{J'aw}_{NO}$ is illustrated in FIG. 12c in the absence or presence of axial diffusion; T denotes the trumpet model in the absence of axial diffusion; T-AD denotes the trumpet model in the presence of axial diffusion. E denotes each individual data point from model T; F denotes each individual data point from model T-AD. Bars represent the mean. The sign § denotes a statistically significant difference among models (paired t-test, P<0.05). The asterisk sign * denotes a statistically significant difference between air and heliox (paired t-test, P<0.05).
Figure 12B:
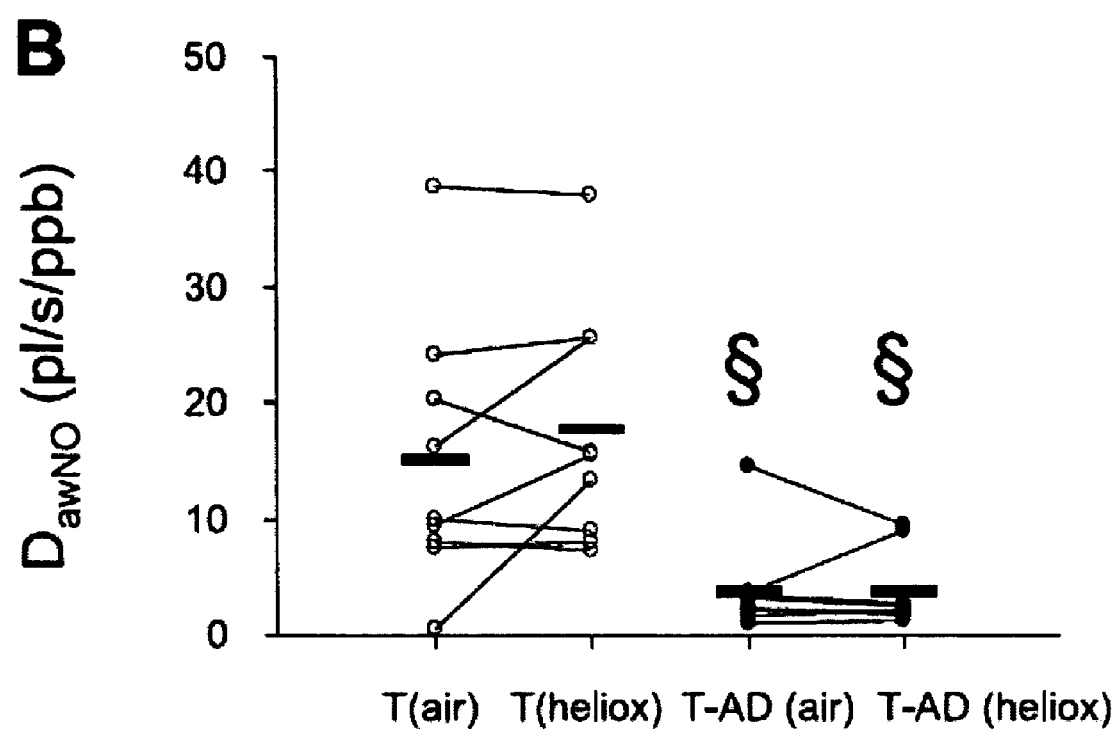
Figure 12C:
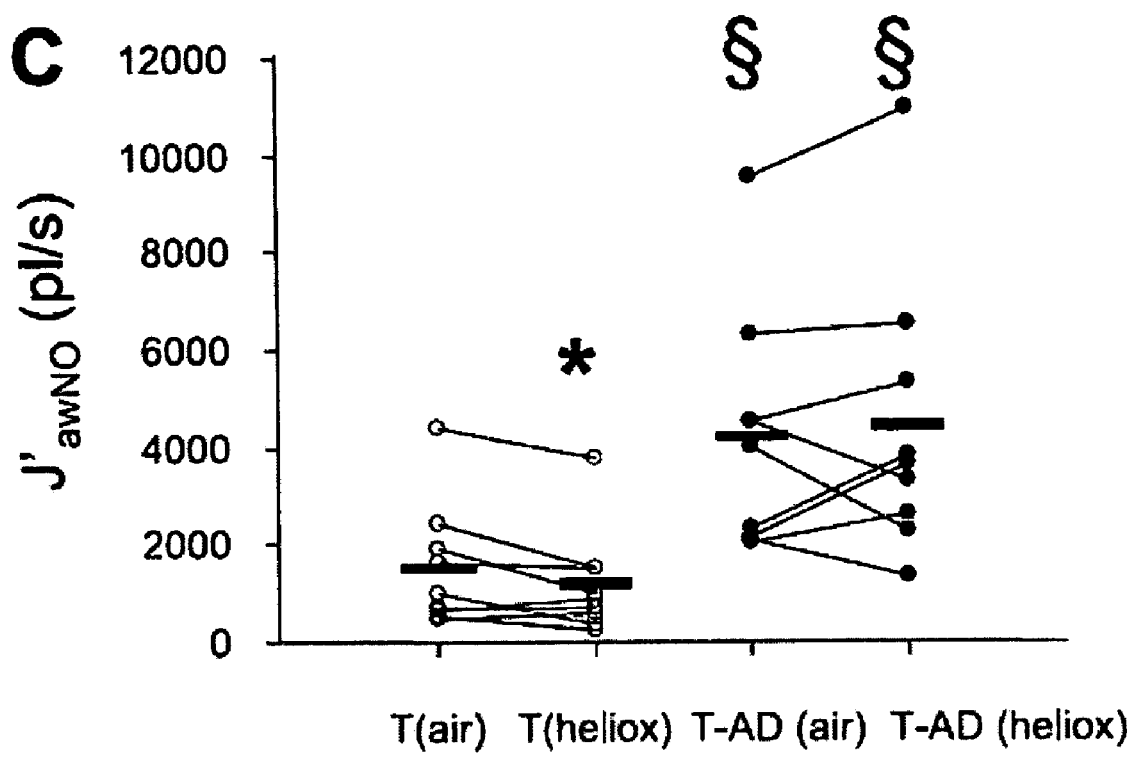

The determined airway wall NO parameters using a model which accounted for or neglected axial diffusion (T and T-AD) are presented in FIGS. 12a-12c for both air and heliox. Both models can accurately simulate the increase in $A_{I,II}$ with increasing breathhold time. For air, the maximum deviation between $A^*_{I,II}$ and $A_{I,II}$ for any of the breath-hold times were 14.9 and 18.6% for T and T-AD, respectively. $R^2$ (coefficient of determination) values were 0.92 and 0.96 for T and T-AD, respectively. For heliox, the maximum deviation between $A^*_{I,II}$ and $A_{I,II}$ for any of the breath-hold times were 10.9 and 11.2% for T and T-AD, respectively, and $R^2$ values were 0.92 and 0.97.

The impact of axial diffusion for the trumpet geometry (T-AD) was substantial. For air, $Caw_{NO}$ and $J'aw_{NO}$ were significantly (P<0.001 for $Caw_{NO}$ and P<0.003 for $J'aw_{NO}$) increased by more than eightfold and threefold, respectively; $Daw_{NO}$ was (P<0.06) decreased by about 75%. For heliox, $Caw_{NO}$ and $J'aw_{NO}$ were also significantly (P<0.001 for $Caw_{NO}$ and P<0.001 for $J'aw_{NO}$) increased by more than 22-fold and 4-fold, respectively; $Daw_{NO}$ was (P<0.005) decreased by about 80%. Of note is the observation that determined airway wall parameters are independent of the insufflating gas when axial diffusion is included in the model (i.e., T-AD).

Figure 13:
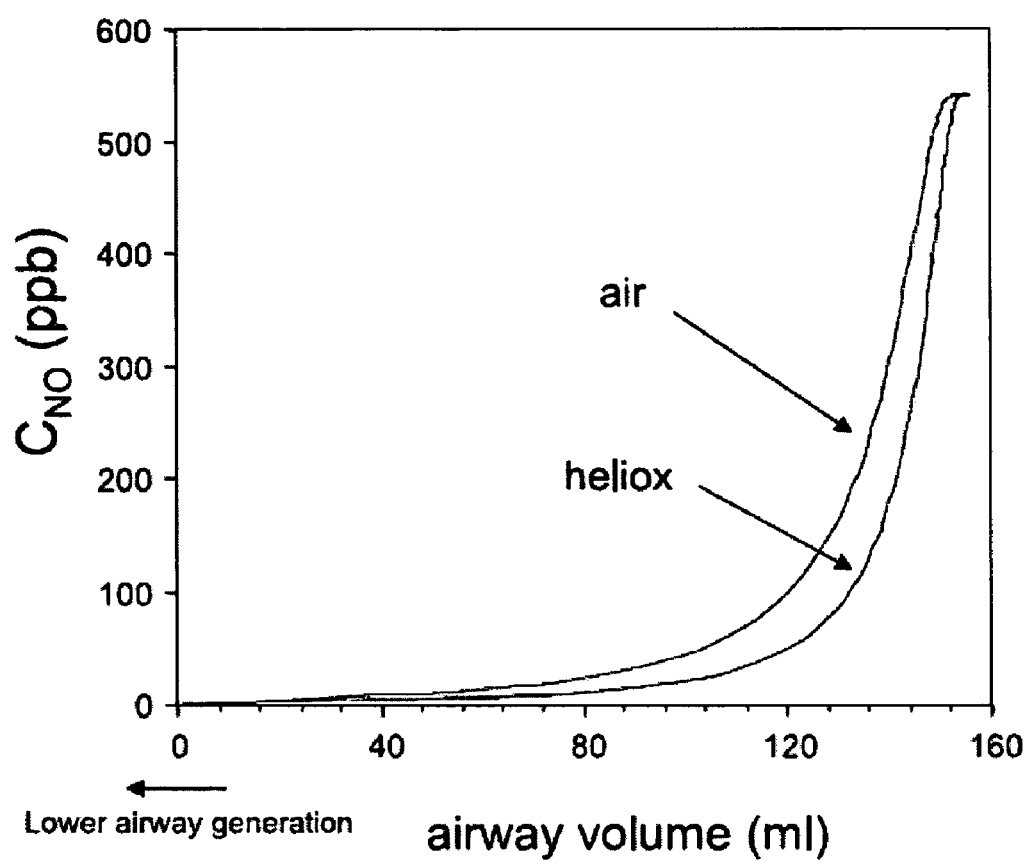
FIG. 13 is a graph of $C_{NO}$ as a function of volumetric position in the airway tree is shown for the T-AD model for both air and heliox breathing when breath-hold time was set to 30 s. $\text{Caw}_{NO}$ was 1,439 ppb and $\text{Daw}_{NO}$ was 3.70 pl s$^{-1}$ ppb$^{-1}$ for the simulation and represented the mean values of the nine healthy subjects when breathing air. The presence of heliox (by changing the molecular diffusivity of NO from 0.23 to 0.52 cm$^2$/s) reduces the concentration of NO along the airway tree during breath hold but does not impact the maximum concentration of the NO within the airway.

NO concentration as a function of airway volumetric position is shown in FIG. 13 for the T-AD model for both air and heliox breathing when breath-hold time was set to 30 s. Recall, for both cases, that total mass of NO within the airway tree is not different because this is the experimental variable for which the determined model parameters are chosen to match. Because estimated NO parameters do not depend on the insufflating gas for model T-AD, the mean parameter set determined from air (1,439 ppb for $Caw_{NO}$ and 3.70 pl s$^{-1}$ ppb$^{-1}$ for $Daw_{NO}$) was used to generate the NO profile within the airway tree. The presence of heliox reduces the concentration of NO along the airway tree during breath hold but does not impact $C_{NO}$ peak.

Figure 14A:
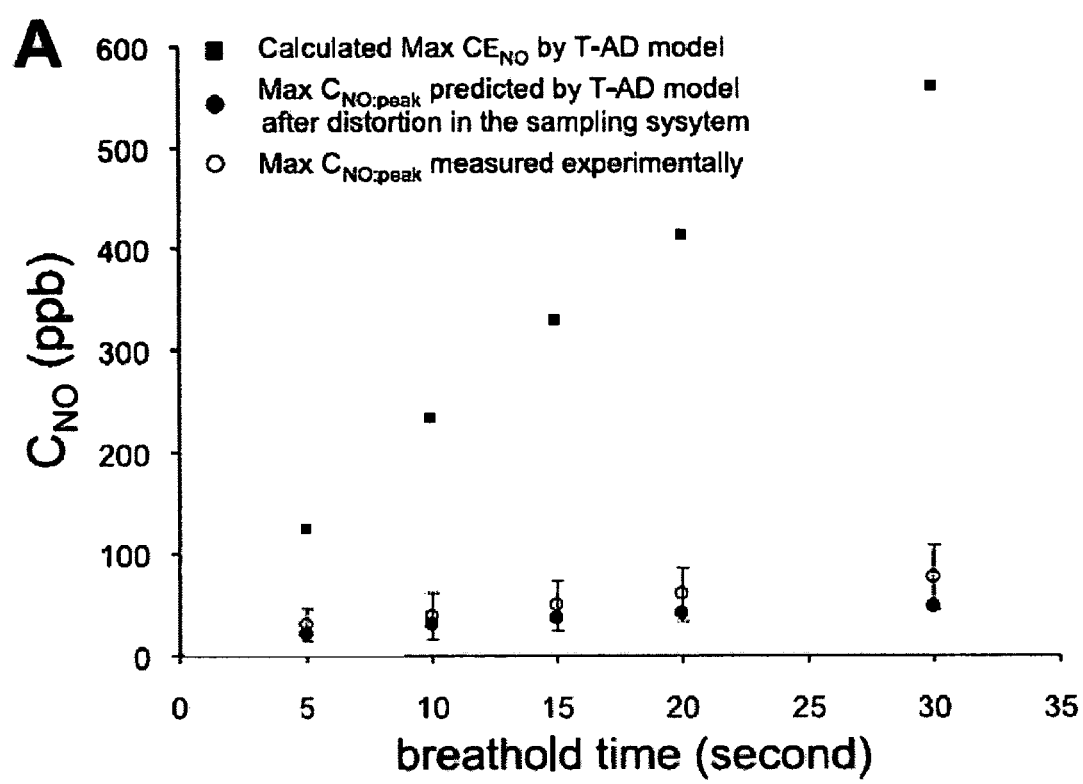
FIGS. 14a and 14b are graphs which illustrate the maximum NO concentrations in the exhaled profile for three cases at each breath-hold time. The symbol ■, is the calculated maximum NO concentration exiting the mouth ($\text{Ce}_{NO}$; i.e., model prediction of peak NO concentration in expired gas) using mean values for best fit, airway wall parameters for air ($\text{Daw}_{NO}$=3.70 pl s$^{-1}$ ppb$^{-1}$, $\text{Caw}_{NO}$=1,439 ppb in FIG. 14a) and heliox ($\text{Daw}_{NO}$=3.56 pl s$^{-1}$ ppb$^{-1}$, $\text{Caw}_{NO}$=1,503 ppb in FIG. 14b); F denotes the model prediction of the maximum $C_{NO\ obs}$ ($C_{NO}$ peak) in expired gas after distortion: in the sampling system, on the basis of composite experimental NO tracing responses; E denotes observed maximum NO concentration in expired gas ($C_{NO\ peak}$). $\text{Ce}_{NO}$ enters the sampling system, which significantly flattens and broadens the exhaled profile because of dispersion introduced within the plumbing, leading to the analytical instrument, where the $C_{NO\ obs}$ is actually measured. The result is a reduction in the peak height of $C_{NO\ obs}$, compared with $\text{Ce}_{NO}$.
Figure 14B:
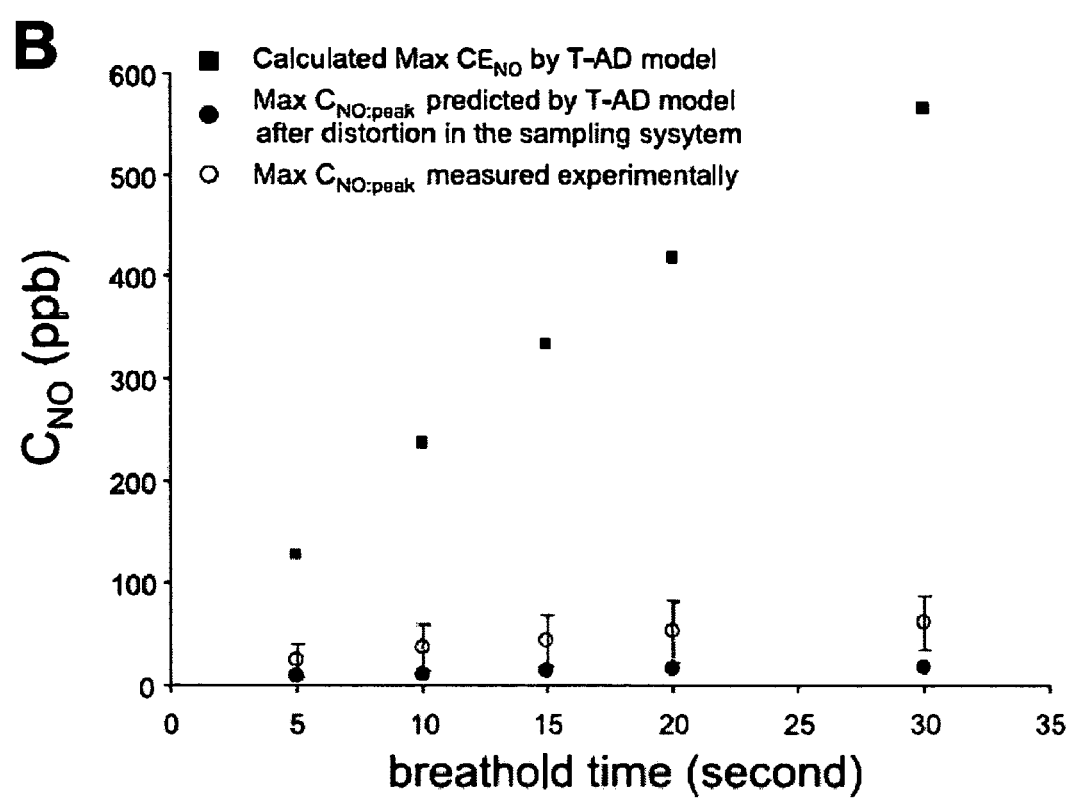

During exhalation, the NO concentration profile in the airway tree exits the mouth and enters the sampling system. $Ce_{NO}$ represents the NO concentration exiting the mouth, whereas $C_{NO\ obs}(t)$ represents the observed NO concentration by the instrument. As previously reported, $C_{NO\ obs}(t)$ predicted by the model determined airway wall NO parameters (mean for all nine subjects, shown in FIGS. 14a and 14b) for T-AD (solid circles, calculated on the basis of experimental NO tracing results described below agrees well with that observed experimentally (open circles) for both air in FIG. 14a and heliox breathing in FIG. 14b. Although the total mass of NO exhaled from the airway tree is not changed, the maximum $C_{NO\ obs}(t)$ (i.e., $C_{NO\ peak}$) is only 9-16% of the maximum $Ce_{NO}$ for air and only 3-6% for heliox breathing, depending on the breathhold time.

Figure 15A:
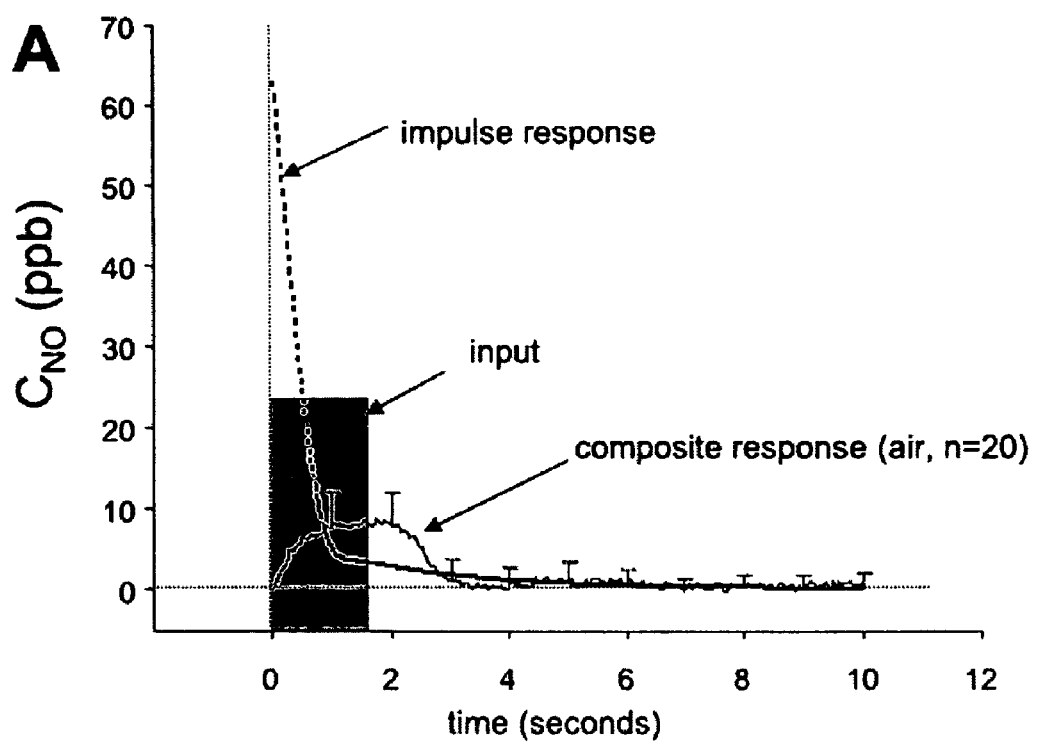
FIGS. 15a and 15b are graphs showing the results of NO tracer analysis for air in FIG. 15a and heliox in FIG. 15b. Experimental data for the composite response (solid lines, average, on the basis of 20 nitric oxide pulse tracings, with error bars representing standard deviation), estimated input (gray shaded regions), and calculated impulse response (dashed lines) were used to compute peak ratios from both air and heliox, composite, breath-hold tracings.
Figure 15B:
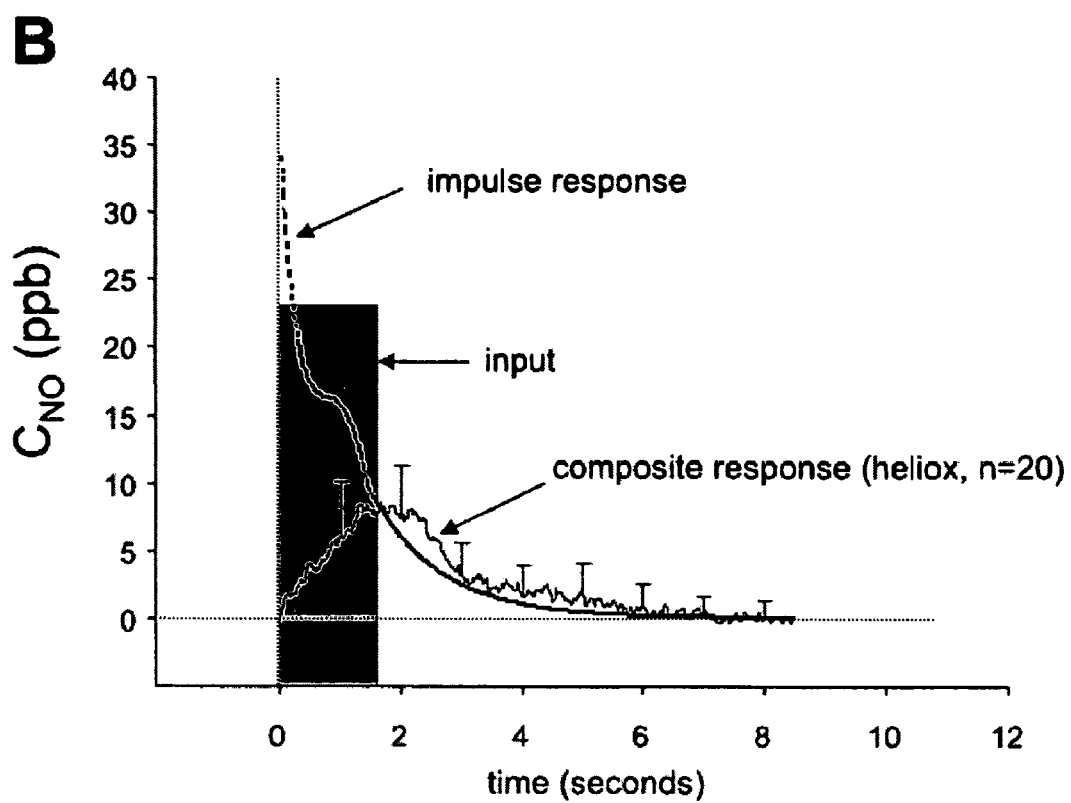

Turn for a moment and consider distortion of no exhalation profile by the sampling system. We performed a tracer study to investigate distortion of NO exhalation profiles by the sampling system (including the mouthpiece and sampling line). We injected 0.2 ml of 45 ppm NO (at a constant rate, over 1.56 s) into a diluent gas stream (about 250 ml/s of either air or heliox). We then monitored the output response (solid lines, shown in FIGS. 15a and 15b, representing the averages of 20 NO tracings), which was significantly flattened and broadened for both air (mean $C_{NO}$ peak reduction of 48%, see FIG. 15a) and heliox (mean $C_{NO}$ peak reduction of 42%; see FIG. 15b). These results were sufficient to compute the impulse response (dashed lines shown in FIGS. 15a and 15b, scaled to yield NO masses equal to the pulse inputs for presentation), which relates the observed output response (measured data) to the expected input. The present sampling system is identical to that described in a previous study. To mimic exhalation by a human subject, the injection was made at the entrance of the mouthpiece (located about 25 cm upstream of the sampling line inlet). From the injection point, the diluent gas first passes through an entrance region (about 50 ml and 2.8-cm diameter) and then enters an in-line filter (about 40 ml and 7-cm diameter) and traverses an exit region (about 75 ml and 2.8-cm diameter) before it reaches the sampling point. We assumed that the injected NO was relatively well mixed within the entrance region, upstream of the filter. Thus we approximated the NO profile near the mouthpiece entrance as a 1.56-s duration stepwise, pulse ("square-wave") input (see gray shaded regions of FIGS. 15a and 15b). To check this assumption, we considered alternate orientations for administering the 45 ppm NO into the diluent gas stream and confirmed that these alternatives had little effect upon the measured response.

The scaled, impulse responses (shown in FIGS. 15a and 15b) were normalized to compute the "unit impulse responses" (transfer functions) for both air and heliox, on the basis of the tracer experiments. These transfer functions were then applied to the fitted T-AD model to predict the expected output response, on the basis of composite data for all nine subjects (see FIGS. 14a and 14b), which resulted in a potential $C_{NO\,peak}$ reduction of 6- to 30-fold.

These results should be interpreted prudently, because significant background noise limits resolution of the impulse response, which is based on composite averages of 20 tracer experiments and does not consider variation between these experiments. Furthermore, input NO profiles predicted by the fitted T-AD model are very sharp (0.1- to 0.2-s duration), compared with the tracer experiments (1.56-s duration), which leads to a much more significant reduction in $C_{NO}$ peak. An alternative approach to the tracer results would be to deconvolve the NO concentration vs. time measurements from the breath-hold experiments directly, which would yield experimental estimates of $C_{NO}$ peak values (independent of any pulmonary model).

Finally, our assumption of a square-wave input (which may actually have been distorted at the mouthpiece entrance) for the tracer study could have resulted in overcorrection for $C_{NO}$ peak (the estimated exhaled peaks), on the basis of the fitted T-AD model. This would partially explain some of the discrepancies in FIGS. 14a and 14b, because $C_{NO}$ peak values predicted by the model (i.e., model predictions of peak NO in expired gas after distortion in the sampling system, denoted by solid circles in FIGS. 14a and 14b) are lower than the observed $C_{NO}$ peak values (i.e., observed peak NO in expired gas, denoted by open circles in FIGS. 14a and 14b).

The above embodiment characterized airway wall NO exchange dynamics using the above disclosed developed breath-hold technique that can more accurately determine the airway wall parameters ($Caw_{NO}$, $Daw_{NO}$, and $J'aw_{NO}$), in particular $Daw_{NO}$. The airway NO parameters should be independent of the physical properties of the insufflating gas (e.g., molecular diffusion coefficient) because they describe features of the airway wall or tissue. We utilized a trumpet model of the airway tree that considers axial diffusion of NO in the gas phase and demonstrated that a single set of airway wall parameters could simulate NO exchange dynamics with either air or heliox as the insufflating gas. We conclude that a trumpet model of the airway tree that considers axial diffusion captures the essential features of NO exchange in the airways. In addition, our results confirm earlier reports that loss of NO from the airways to the alveolar region by axial diffusion profoundly impacts airway wall NO characterization and that the airway wall concentration is more than an order of magnitude larger than previous estimates in healthy adults utilizing models that neglected axial diffusion and the trumpet geometry of the airways.

Consider now the Impact of using insufflating gas. When heliox was used as the insufflating gas in the present study, exhaled NO concentration and thus the total mass of NO exhaled. ($A_{I,II}$) was decreased in FIGS. 10a-10c and 11a-11d. The reduced $A_{I,II}$ is due primarily to the reduced $W_{50}$ (thinner peak causes a small area) because $C_{NO\,peak}$ is independent of the insufflating gas as shown in FIGS. 10a-10c. Molecular diffusion of NO in helium is enhanced relative to nitrogen. Thus, in the presence of heliox, the rate of molecular diffusion of NO is increased 2.3-fold. The reduced $W_{50}$ represents depletion of NO in the smaller airways due to enhanced axial diffusion of NO from the airways to the alveolar region. $C_{NO}$ peak occurs in the first part of the exhaled breath, which is far away from the sink (i.e., the alveolar region) and is therefore not impacted by altering the rate of axial diffusion. This result is consistent with the concentration profile of NO in the airway tree as predicted by the trumpet model in FIG. 13.

$V_{I,II}$ represents the volume of phase I and II of the exhaled profile as defined by the point of zero slope in the exhalation profile as shown in FIG. 10a and is therefore an estimate of that point in the exhalation when all airway gas has been expired by convection, including that in the respiratory transition region (i.e., generations 18-23). $V_{I,II}$ was statistically reduced in the presence of heliox for two of the five breath-hold times in FIG. 11c, and thus this trend may also explain the reduced $A_{I,II}$ observed for heliox. The trumpet model describes an abrupt transition between the airway and alveolar region, and this boundary is at a fixed concentration of $Ca_{NO}=0$. Thus the trumpet model structure, including the boundary conditions, dictates that a zero slope occurs at an exhaled volume equal to the volume of the trumpet as in FIG. 13 and that this volume would be independent of the insufflating gas. However, it is also evident from FIG. 13 that the slope of the concentration profile becomes flatter at smaller volumes in the presence of heliox because of enhanced loss of NO to the alveolar region. This observation, combined with normal experimental noise and the fact that an abrupt transition between the airways and the alveolar region does not occur, may account for the experimental observations.

As shown in FIGS. 12a-12c, airway wall NO parameters depend strongly on the insufflating gas when axial diffusion is neglected in the model (model T). In contrast, when axial diffusion is included (model T-AD), the airway wall NO parameters are independent of the insufflating gas. The airway wall NO parameters describe the airway wall tissue and depend on such characteristics as wall surface area, tissue thickness, and net rate of tissue production. Thus determined values for the airway wall NO parameters should be independent of the properties of the gas phase, such as the molecular diffusion coefficient. Indeed, we have previously demonstrated theoretically that the rate of radial diffusion of NO from the airway wall is independent of the gas phase. Our result suggests that a model of the airways that considers both trumpet geometry and axial diffusion captures the essential features of airway NO exchange.

Consider the validity of the model assumptions and structure. We assume that as z approaches zero, exhaled NO concentration in the gas phase of the airways ($C_{NO}$) approaches the steady-state alveolar concentration, $Ca_{NO}$ in FIG. 3b. Although $Ca_{NO}$ has been shown by many investigators to be nonzero, the values are generally <2 ppb, much lower than those observed in the airway tree during the breath hold. Thus, for simplicity, $Ca_{NO}$ is set to zero as one of the boundary conditions. Others in the prior art have also explored the impact of axial diffusion of NO exchange by accounting for the trumpet shape of the airway tree. In the prior art simulation, a zero $Ca_{NO}$ had minimal impact on the estimated steady-state NO concentration at 50 ml/s exhalation flow compared with $Ca_{NO}$=1.8 ppb (28.7 ppb vs. 29.8 ppb, respectively). Thus setting $Ca_{NO}$ to zero in the present simulation should have a minimal impact on the airway wall NO parameters.

The molecular diffusivity of NO (0.52 $cm^2$/s in heliox and 0.23 $cm^2$/s in air) is an approximate value and is assumed to be maintained in the airway trumpet (up to generation 17) during the breath hold. The molecular diffusivity of NO in the alveolar space is likely to be somewhere between these two values as the inspired heliox mixes with air in the residual volume. However, the fact that a pre-breath-hold tidal breathing wash-in period of heliox for 2 min has been shown not to impact exhaled NO concentrations suggests that the rate-limiting location of axial diffusion for NO during the breath hold is not in the residual volume and alveolar space, but rather exists in small airways.

Accumulation of NO in the airway space during filling and evacuation of the airway tree before and after the breath hold may introduce error, which our model and parameter estimation algorithm do not consider. However, the subjects were instructed to inspire rapidly, generally over the course of <3 s, and thus maintained an average inspiration flow of >1 l/s. Thus filling of the airway tree at the end of inspiration would generally take <0.2 s and could be considered negligible. The exhalation flow was recorded and was >200 ml/s [e.g., experimental average flow rate (SD) after the 20-s breath hold of air was 229 ml/s (SD 44)] to ensure evacuation of the airway space in about 2 s. This delay may introduce an error, especially at the shorter breath-hold time (5 s). However, the 2-s delay would only be observed for the last part of the airway volume; thus the mean delay in the exhalation would be even smaller and is likely to be negligible.

Turn now to tissue phase concentration. Our estimated mean $Caw_{NO}$ in healthy adults is about 1,500 ppb (1,439 and 1,503 ppb for air and heliox, respectively), which is more than an order of magnitude larger than that predicted by models that neglect axial diffusion and the shape of the airway tree, but consistent with our previous report using the breathholding technique. This higher concentration approaches that capable of modulating smooth muscle tone. It has recently been demonstrated that soluble guanylate cyclase, the enzyme responsible for smooth muscle dilation, can be activated at NO concentrations as low as 3 ppm (about 5 nM). Thus, in asthma, in which exhaled NO concentrations can be increased by more than fivefold, airway wall concentrations may reach levels that impact airway and vascular smooth muscle tone.

During a breath hold, the concentration of NO in the airways increases because the concentration in the tissue phase (i.e., wall concentration, $Caw_{NO}$) is larger than the gas phase. For a very long breath-hold time, the gas phase concentration, $C_{NO}$, would eventually reach $Caw_{NO}$. Our estimated mean $Caw_{NO}$ in healthy adults is much larger than the experimentally observed peak concentration of 77 and 62 ppb for air and heliox, respectively, after the largest breath-hold time of 30 s. This observation is consistent with our previous work, and the discrepancy is due to two phenomena.

First, the sampling system introduces significant distortion of the observed exhaled profile due to axial dispersion (non-ideal flow) of the gas within the mouthpiece assembly and sampling line leading to the NO analyzer. This causes a pulse of NO to be significantly flattened (thus lowering the peak concentration) and broadened without altering the total mass of NO in the peak. This phenomenon was assessed theoretically in previous studies, which accounted for axial dispersion within the sampling line. Herein, we have accounted for this effect experimentally as discussed above. As presented in FIGS. 14a and 14b, $C_{NO\ obs}(t)$ predicted by the T-AD model was calculated on the basis of experimental composite responses (n=20) of NO tracings for both air and heliox as the carrier gas. These results are in good agreement with our experimental measurements for both air and heliox breathing. However, $C_{NO\ obs}(t)$ predicted by model T-AD generates slightly lower values compared with experimentally observed $C_{NO}$ peak, which may be a consequence of averaging 20 experimental NO tracings to determine the composite responses. Other possible explanations are limitations on the precision of the tracer study as discussed above or that $Caw_{NO}$ could be higher in the upper portion of the airway than in the lower airway.

The second reason why the observed gas concentration is less than $Caw_{NO}$ is due to the observation that a steady state (or equilibrium) has not been reached with the gas phase. This can be observed by simply noting that $C_{NO}$ peak after a 30-s breath hold time is significantly larger than that after the 20-s breathhold time. The estimated mean time to reach 95% of equilibrium (i.e., $Caw_{NO}$) is 128 s (2.13 min) for air and 218 s (3.63 min) for heliox breathing from the T-AD model. The longer time in the presence of heliox is a direct result of the enhanced loss of NO to the alveolar region, resulting in a smaller net (i.e., flux of the airway wall minus flux into the alveolar region) flux of NO into the gas phase.

In conclusion, utilizing a newly developed technique based on progressively increasing breath-hold times, this study investigated the impact of altering the properties of the insufflating gas on airway NO exchange. In the presence of heliox, the rate of NO diffusion is enhanced 2.3-fold and results in enhanced loss of airway NO to the alveolar region. A trumpet model that considers axial diffusion is able to accurately simulate this effect and predict airway NO exchange parameters in healthy adults that characterize airway wall tissue and are independent of the insufflating gas. A result of this model is the determination of airway wall concentrations in healthy adults that exceed 1 ppm, which is approximately an order of magnitude larger than estimates made with models that neglect the trumpet geometry and axial diffusion. This concentration approaches that capable of modulating airway smooth muscle tone and thus may be of clinical interest in disease states such as asthma that have elevated exhaled NO. We conclude that accurate estimation of flow-independent airway NO exchange parameters must include mathematical models that consider axial diffusion of NO in the gas phase and the trumpet shape of the airway tree.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more, elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method to characterize NO gas exchange dynamics in human lungs comprising:
    performing a series of breath hold maneuvers of progressively increasingly breath hold times, each breath hold maneuver comprising inhaling a gas, holding a breath for a selected time duration, and exhaling at a flow rate which is uncontrolled but which is effective to ensure evacuation of the airway space; and
    measuring airway NO parameters during consecutive breath hold maneuvers,
    whereby disease states of the lungs are diagnosed using the measured airway NO parameters.

2. The method of claim 1 further comprising maintaining a predetermined positive pressure during the breath hold and exhalation to prevent nasal contamination of the measured airway NO parameters.

3. The method of claim 2 where maintaining a predetermined positive pressure during the breath hold and exhalation to prevent nasal contamination comprises maintaining a positive pressure of 5 cm $H_2O$ or more.

4. The method of claim 1 where exhaling at a flow rate evacuates the airway space in 2 seconds or less.

5. The method of claim 1 where exhaling at a flow rate evacuates the airway space comprises exhaling at a rate of 300 ml/s or more.

6. The method of claim 1 where performing the series of breath hold maneuvers of progressively increasingly breath hold times comprises performing a series of breath hold maneuvers with breath hold times of having increasing durations of 5 seconds over the previous breath hold.

7. The method of claim 1 where performing the series of breath hold maneuvers with breath hold times of having increasing durations of 5 seconds over the previous breath hold comprises performing a series of breath hold maneuvers with breath hold times of having 5-, 10-, 15-, 20-, and 30-second breath holds.

8. The method of claim 1 where measuring airway NO parameters during consecutive breath hold maneuvers comprises measuring the indexes of NO exchange dynamics and spirometry.

9. The method of claim 8 where measuring spirometry comprises measuring forced vital capacity and forced expiratory volume in 1 second.

10. The method of claim 8 where exhalation is characterized as comprised of three temporal phases I, II, and II and where measuring the indexes of NO exchange dynamics and spirometry comprises measuring:
    maximum observed concentration of NO, $C_{peakNO}$,
    width of phases I and II of exhalation, $W_{50}$,
    total exhaled volume of NO during phases I and II, $V_{I,II}$, and/or
    total mass or volume of NO in phases I and II, $A_{I,II}$.

11. The method of claim 1 where a model of an entire airway tree of the lungs is assumed and further comprising:
    determining diffusing capacity of NO in an entire airway tree of the lungs, $Daw_{NO}$;
    determining airway wall concentration of NO, $Caw_{NO}$; and/or
    determining maximum total volumetric flux of NO from the entire airway tree, $J'aw_{NO}$ from the measured airway NO parameters.

12. The method of claim 10 where a model of an entire airway tree of the lungs is assumed and further comprising:
    determining using the model diffusing capacity of NO in an entire airway tree of the lungs, $Daw_{NO}$;
    determining using the model airway wall concentration of NO, $Caw_{NO}$; and/or
    determining using the model maximum total volumetric flux of NO from the entire airway tree, $J'aw_{NO}$ from the measured airway NO parameters.

13. The method of claim 12 where the assumed model of an entire airway tree of the lungs comprises a model including a trumpet geometry of the airway of the lungs and gas phase axial diffusion of NO occurs.

14. The method of claim 1 where inhaling a gas comprises inhaling heliox.

15. The method of claim 14 where inhaling heliox comprises inhaling a sufficient amount of heliox to enhance NO diffusion in the lungs to a level sufficient to modulate airway smooth muscle tone.

16. The method of claim 15 where inhaling a sufficient amount of heliox to enhance NO diffusion in the lungs to a level sufficient to modulate airway smooth muscle tone comprises inhaling sufficient amounts of heliox to activate soluble guanylate cyclase in airway smooth muscle tissue.

17. An apparatus for characterizing NO gas exchange dynamics in human lungs comprising:
    means for performing a series of breath hold maneuvers of progressively increasingly breath hold times, each breath hold maneuver comprising means for inhaling a gas, means for holding a breath for a selected time duration, and means for exhaling at a flow rate which is uncontrolled but which is effective to ensure evacuation of the airway space; and means for measuring airway NO parameters during consecutive breath hold maneuvers, whereby disease states of the lungs are diagnosed using the measured airway NO parameters.

18. The apparatus of claim 17 further comprising means for maintaining a predetermined positive pressure during the breath hold and exhalation to prevent nasal contamination of the measured airway NO parameters.

19. The apparatus of claim 18 where the means for maintaining a predetermined positive pressure during the breath hold and exhalation to prevent nasal contamination comprises means for maintaining a positive pressure of 5 cm $H_2O$ or more.

20. The apparatus of claim 17 where the means for exhaling at a flow rate evacuates the airway space in 2 seconds or less.

21. The apparatus of claim 17 where the means for exhaling at a flow rate evacuates the airway space comprises means for exhaling at a rate of 300 ml/s or more.

22. The apparatus of claim 1 where the means for performing the series of breath hold maneuvers of progressively increasingly breath hold times comprises means for performing a series of breath hold maneuvers with breath hold times of having increasing durations of 5 seconds over the previous breath hold.

23. The apparatus of claim 17 where the means for performing the series of breath hold maneuvers with breath hold times of having increasing durations of 5 seconds over the previous breath hold comprises means for performing a series of breath hold maneuvers with breath hold times of having 5-, 10-, 15-, 20-, and 30-second breath holds.

24. The apparatus of claim 17 where the means for measuring airway NO parameters during consecutive breath hold maneuvers comprises means for measuring the indexes of NO exchange dynamics and spirometry.

25. The apparatus of claim 24 where the means for measuring spirometry comprises means for measuring forced vital capacity and forced expiratory volume in 1 second.

26. The apparatus of claim 24 where exhalation is characterized as comprised of three temporal phases I, II, and II and where the means for measuring the indexes of NO exchange dynamics and spirometry comprises means for measuring:

maximum observed concentration of NO, $C_{peakNO}$, width of phases I and II of exhalation, $W_{50}$, total exhaled volume of NO during phases I and II, $V_{I, II}$, and/or total mass or volume of NO in phases I and II, $A_{I, II}$.

27. The apparatus of claim 17 where a model of an entire airway tree of the lungs is assumed and further comprising:

means for determining diffusing capacity of NO in an entire airway tree of the lungs, $Daw_{NO}$;

means for determining airway wall concentration of NO, $Caw_{NO}$; and/or means for determining maximum total volumetric flux of NO from the entire airway tree, $J'aw_{NO}$ from the measured airway NO parameters.

28. The apparatus of claim 26 where a model of an entire airway tree of the lungs is assumed and further comprising:

means for determining using the model diffusing capacity of NO in an entire airway tree of the lungs, $Daw_{NO}$;

means for determining using the model airway wall concentration of NO, $Caw_{NO}$; and/or means for determining using the model maximum total volumetric flux of NO from the entire airway tree, $J'aw_{NO}$ from the measured airway NO parameters.

29. The apparatus of claim 28 where the assumed model of an entire airway tree of the lungs comprises a model including a trumpet geometry of the airway of the lungs and gas phase axial diffusion of NO occurs.

30. The apparatus of claim 17 where the means for inhaling a gas comprises means for inhaling heliox.

31. The apparatus of claim 30 where the means for inhaling heliox comprises means for inhaling a sufficient amount of heliox to enhance NO diffusion in the lungs to a level sufficient to modulate airway smooth muscle tone.

32. The apparatus of claim 31 where the means for inhaling a sufficient amount of heliox to enhance NO diffusion in the lungs to a level sufficient to modulate airway smooth muscle tone comprises means for inhaling sufficient amounts of heliox to activate soluble guanylate cyclase in airway smooth muscle tissue.

* * * * *